United States Patent [19]
Elliott et al.

[11] Patent Number: 5,885,999
[45] Date of Patent: Mar. 23, 1999

[54] SERINE DERIVATIVES AND THEIR USE AS THERAPEUTIC AGENTS

[75] Inventors: Jason Matthew Elliott, Knockholt; Angus Murray MacLeod, Bishops Stortford; Graeme Irvine Stevenson, Saffron Walden, all of England

[73] Assignee: Merck Sharp & Dohme Ltd., Hoddesdon, England

[21] Appl. No.: 786,522

[22] Filed: Jan. 21, 1997

[30] Foreign Application Priority Data

Jan. 29, 1996 [GB] United Kingdom .................. 9601724

[51] Int. Cl.⁶ .................. C07D 239/02; C07D 211/06; A61K 31/445; A61K 31/505
[52] U.S. Cl. .................. 514/258; 514/319; 544/298; 544/300; 546/192; 546/205; 546/206
[58] Field of Search .................. 546/192, 205, 546/206; 514/319, 258; 544/298, 300

[56] References Cited

U.S. PATENT DOCUMENTS

| | | | |
|---|---|---|---|
| 5,346,907 | 9/1994 | Kerwin, Jr. et al. | 514/312 |
| 5,536,716 | 7/1996 | Chen et al. | 514/215 |

FOREIGN PATENT DOCUMENTS

| | | |
|---|---|---|
| 0 360 390 | 3/1990 | European Pat. Off. |
| 675122 | 10/1995 | European Pat. Off. |
| WO 94/29309 | 12/1994 | WIPO |
| 95/15319 | 6/1995 | WIPO |
| 96/05203 | 2/1996 | WIPO |
| 96/39384 | 12/1996 | WIPO |
| 97/15573 | 5/1997 | WIPO |

*Primary Examiner*—S. Mark Clardy
*Assistant Examiner*—Sabiha N. Qazi
*Attorney, Agent, or Firm*—Philippe L. Durette; Melvin Winokur

[57] ABSTRACT

The present invention relates to compounds of formula (I):

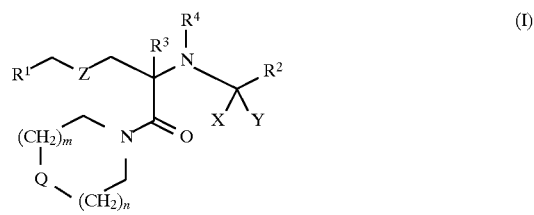

wherein m is zero, 1 or 2; and n is zero or 1, with the proviso that the sum total of m+n is 1 or 2;

$R^1$ represents phenyl; naphthyl; benzhydryl; or benzyl, where the naphthyl group or any phenyl moiety may be substituted;

$R^2$ represents hydrogen; phenyl; heteroaryl selected from indazolyl, thienyl, furanyl, pyridyl, thiazolyl, tetrazolyl and quinolinyl; naphthyl; benzhydryl; or benzyl; wherein each heteroaryl, the naphthyl group and any phenyl moiety may be substituted;

$R^3$ and $R^4$ each independently represents hydrogen or $C_{1-6}$alkyl or $R^3$ and $R^4$ together are linked so as to form a $C_{1-3}$alkylene chain;

Q represents $CR^5R^6$ or $NR^5$;

X and Y each independently represents hydrogen, or together form a group $=O$; and Z represents a bond, O, S, SO, $SO_2$, $NR^c$ or $-(CR^cR^d)-$, where $R^c$ and $R^d$ each independently represent hydrogen or $C_{1-6}$alkyl;

or a pharmaceutically acceptable salt thereof.

The compounds are of particular use in the treatment or prevention of pain, inflammation, migraine, emesis and postherpetic neuralgia.

19 Claims, No Drawings

SERINE DERIVATIVES AND THEIR USE AS THERAPEUTIC AGENTS

This invention relates to a class of azacyclic compounds, which are useful as tachykinin antagonists. More particularly, the compounds of the invention comprise a substituted piperidine or piperazine moiety and a substituted serine derived moiety.

The tachykinins are a group of naturally occurring peptides found widely distributed throughout mammalian tissues, both within the central nervous system and in peripheral nervous and circulatory systems.

The tachykinins are distinguished by a conserved carboxyl-terminal sequence:

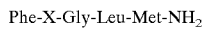

Phe-X-Gly-Leu-Met-NH₂

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6 (suppl. 3), 237–242). The current nomenclature designates the three tachykinin receptors mediating the biological actions of substance P, NKA and NKB as the NK₁, NK₂ and NK₃ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti,*J. Auton. Pharmacol.* (1993) 13, 23–93.

For instance, substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" *TIPS* (1987) 8, 506–510], specifically in the transmission of pain in migraine (B. E. B. Sandberg et al, *J. Med Chem,* (1982) 25, 1009) and in arthritis [Levine et al in *Science* (1984) 226, 547–549]. Tachykinins have also been implicated in gastrointestinal (GI) disorders and diseases of the GI tract such as inflammatory bowel disease [Mantyh et al in *Neuroscience* (1988) 25(3), 817–37 and D. Regoli in "Trends in Cluster Headache" Ed. Sicuteri et al Elsevier Scientific Publishers, Amsterdam (1987) page 85)] and emesis [F. D. Tattersall et al, *Eur. J. Pharmacol.,* (1993) 250, R5–R6]. It is also hypothesised that there is a neurogenic mechanism for arthritis in which substance P may play a role [Kidd et al "A neurogenic Mechanism for Symmetrical Arthritis" in *The Lancet,* 11 Nov. 1989 and Gröblad et al, "Neuropeptides in Synovium of Patients with Rheumatoid Arthritis and Osteoarthritis" in *J. Rheumatol.* (1988) 15(12), 1807–10]. Therefore, substance P is believed to be involved in the inflammatory response in diseases such as rheumatoid arthritis and osteoarthritis, and fibrositis [O'Byrne et al, *Arthritis and Rheumatism* (1990) 33, 1023–8]. Other disease areas where tachykinin antagonists are believed to be useful are allergic conditions [Hamelet et al, *Can. J. Pharmacol. Physiol.* (1988) 66, 1361–7], immunoregulation [Lotz et al, *Science* (1988) 241, 1218–21 and Kimball et al,*J. Immunol.* (1988) 141(10), 3564–9] vasodilation, bronchospasm, reflex or neuronal control of the viscera [Mantyh et al, *PNAS* (1988) 85, 3235–9] and, possibly by arresting or slowing β-amyloid-mediated neurodegenerative changes [Yankner et al, *Science* (1990) 250, 279–82] in senile dementia of the Alzheimer type, Alzheimer's disease and Down's Syndrome.

Tachykinin antagonists may also be useful in the treatment of small cell carcinomas, in particular small cell lung cancer (SCLC) [Langdon et al, *Cancer Research* (1992) 52, 4554–7].

Substance P may also play a role in demyelinating diseases such as multiple sclerosis and amyotrophic lateral sclerosis [J. Luber-Narod et al, poster C.I.N.P. XVIIIth Congress, 28 Jun.–2 Jul. 1992], and in disorders of bladder function such as bladder detrusor hyper-reflexia (*Lancet,* 16 May 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

In view of their metabolic instability, peptide derivatives are likely to be of limited utility as therapeutic agents. It is for this reason that non-peptide tachykinin antagonists are sought.

In essence, this invention provides a class of potent non-peptide tachykinin antagonists.

The present invention provides a compound of formula (I), or a pharmaceutically acceptable salt thereof:

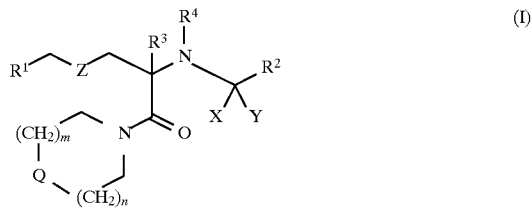

wherein
  m is zero, 1 or 2;
  n is zero or 1, with the proviso that the sum total of m+n is 1 or 2;
  $R^1$ represents unsubstituted phenyl or phenyl substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, —O(CH₂)$_p$O— where p is 1 or 2, halogen, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $COR^a$, $CO_2R^a$ or $CONR^aR^b$, where $R^a$ and $R^b$ each independently represent hydrogen, $C_{1-6}$alkyl, phenyl or trifluoromethyl; naphthyl; benzhydryl; or benzyl, where the naphthyl group or each phenyl moiety of benzyl and benzhydryl may be substituted by $C_{1-6}$alkyl, $C_{1-6}$alkoxy, halogen or trifluoromethyl;

$R^2$ represents hydrogen; unsubstituted phenyl or phenyl substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, —O(CH$_2$)$_p$O— where p is 1 or 2, halogen, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $COR^a$, $CO_2R^a$ or $CONR^aR^b$, where $R^a$ and $R^b$ are as previously defined; heteroaryl selected from indazolyl, thienyl, furanyl, pyridyl, thiazolyl, tetrazolyl and quinolinyl; naphthyl; benzhydryl; or benzyl; wherein each heteroaryl, the naphthyl group and each phenyl moiety of benzyl and benzhydryl may be substituted by $C_{1-6}$alkyl, $C_{1-6}$alkoxy, halogen or trifluoromethyl;

$R^3$ and $R^4$ each independently represents hydrogen or $C_{1-6}$alkyl or $R^3$ and $R^4$ together are linked so as to form a $C_{1-3}$alkylene chain;

Q represents $CR^5R^6$ or $NR^5$;

X and Y each independently represents hydrogen, or together form a group =O;

Z represents a bond, O, S, SO, SO$_2$, $NR^c$ or —$(CR^cR^d)$—, where $R^c$ and $R^d$ each independently represent hydrogen or $C_{1-6}$alkyl;

$R^5$ represents $C_{1-3}$alkyl substituted by a group selected from $OR^a$, $SR^a$, $SOR^a$, $SO_2R^a$, $NR^aR^b$, $NR^aCOR^b$, $NR^aCO_2R^b$, $NR^aSO_2R^b$, $COR^a$, $CO_2R^a$ or $CONR^aR^b$, where $R^a$ and $R^b$ are as previously defined; unsubstituted phenyl; phenyl substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, —O(CH$_2$)$_p$O— where p is 1 or 2, halogen, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $NR^aSO_2R^b$, $COR^a$, $CO_2^a$, $CONR^aR^b$, or $C_{1-3}$alkyl substituted by a group selected from $OR^a$, $SR^a$, $SOR^a$, $SO_2R^a$, $NR^aR^b$, $NR^aCOR^b$, $NR^aCO_2R^b$, $NR^aSO_2R^b$, $COR^a$, $CO_2R^a$ or $CONR^aR^b$, where $R^a$ and $R^b$ are as previously defined; benzimidazol-1-yl; 2-keto-benzimidazol-1-yl; or heteroaryl selected from pyridinyl, pyridazinyl, pyrimidinyl and pyrazinyl, wherein each heteroaryl may be substituted by $C_{1-6}$alkyl, $C_{1-6}$alkoxy, halogen or trifluoromethyl;

$R^6$ represents hydrogen, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, halogen, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $NR^aSO_2R^b$, $COR^a$, $CO_2R^a$, $CONR^aR^b$, or $C_{1-3}$alkyl substituted by a group selected from $OR^a$, $SR^a$, $SOR^a$, $SO_2R^a$, $NR^aR^b$, $NR^aCOR^b$, $NR^aCO_2R^b$, $NR^aSO_2R^b$, $COR^a$, $CO_2R^a$ or $CONR^aR^b$, where $R^a$ and $R^b$ are as previously defined;

or $R^5$ and $R^6$ together are linked so as to form a 5- or 6-membered ring optionally substituted by =O, =S or a $C_{1-4}$alkyl or hydroxy group, and optionally containing a double bond, which ring may optionally contain in the ring one or two heteroatoms selected from O and S, or groups selected from $NR^c$, SO or SO$_2$, where $R^c$ is as previously defined, and to which ring there is fused a benzene or thiophene ring, which benzene or thiophene ring is optionally substituted by 1, 2 or 3 substituents selected from $C_{1-6}$alkyl, $C_{3-7}$cycloalkyl, $C_{3-7}$cycloalkyl$C_{1-4}$alkyl, phenyl$C_{1-4}$alkyl, trifluoromethyl, cyano, $OR^a$, $SR^a$, $SOR^a$, $SO_2R^a$, $NR^aR^b$, $NR^aCOR^b$, $NR^aCO_2R^b$, $NR^aSO_2R^b$, $COR^a$, $CO_2R^a$ or $CONR^aR^b$, wherein the phenyl moiety of a phenyl$C_{1-4}$alkyl group may be substituted by $C_{1-6}$alkyl, $C_{1-6}$alkoxy, halogen or trifluoromethyl, and $R^a$ and $R^b$ are as previously defined.

As used herein, the definition of each expression, when it occurs more than once in any structure, is intended to be independent of its definition elsewhere in the same structure.

The alkyl, alkenyl and alkynyl groups referred to with respect to the formulae herein may represent straight or branched groups. Thus, for example, suitable alkyl groups include methyl, ethyl, n- or iso-propyl and n-, sec-, iso- or tert-butyl. The cycloalkyl groups referred to above may be, for example, cyclopropyl, cyclobutyl, cyclopentyl or cyclohexyl. Similarly, suitable cycloalkylalkyl groups include cyclopropylmethyl. Suitable alkenyl groups include vinyl and allyl; and suitable alkynyl groups include propargyl.

The term "halogen" as used herein includes fluorine, chlorine, bromine and iodine, especially chlorine and fluorine.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

Those compounds according to the invention which contain one or more chiral centres may exist both as enantiomers and as diastereomers. It is to be understood that all such isomers and mixtures thereof are encompassed within the scope of the present invention.

Preferably m is 1 or 2, n is zero or 1 and the sum total of m+n is 2. Most especially, m is 1 and n is 1.

Preferably $R^1$ represents unsubstituted phenyl or phenyl substituted by one or two groups selected from $C_{1-6}$alkyl such as methyl, halogen such as chlorine, fluorine and bromine, and trifluoromethyl. Particularly preferred substituents are chlorine and trifluoromethyl.

Most preferably, $R^1$ represents disubstituted phenyl, in particular 3,4-disubstituted phenyl, especially 3,4-dichlorophenyl.

Suitable values for the group $R^2$ include unsubstituted or substituted phenyl, 5-membered heteroaryl such as thienyl or furanyl, 6-membered heteroaryl such as pyridyl, quinolinyl, naphthyl, and benzhydryl.

Preferably $R^2$ represents unsubstituted or substituted phenyl, especially unsubstituted phenyl.

When $R^2$ represents substituted phenyl it preferably represents dichlorophenyl, especially 3,4-dichlorophenyl.

Preferably $R^3$ and $R^4$ each independently represent hydrogen.

Preferably $R^5$ is $C_{1-3}$alkyl, especially —CH$_2$—, substituted by a group selected from $NR^aCOR^b$, $NR^aSO_2R^b$ or $CO_2R^a$, where $R^a$ and $R^b$ are as previously defined; unsubstituted phenyl; phenyl substituted by a group selected from $C_{1-6}$alkyl, halogen, cyano, nitro, $OR^a$, $NR^aR^b$, $NR^aSO_2R^b$ or $C_{1-3}$alkyl, especially —CH$_2$—, substituted by $NR^aR^b$, $NR^aCOR^b$ or $NR^aSO_2R^b$, where $R^a$ and $R^b$ are as previously defined; 2-keto-benzimidazol-1-yl; pyridinyl, especially pyridin-2-yl; and pyrimidinyl, especially pyrimidin-2-yl.

Preferably $R^6$ is hydrogen, cyano, $NR^aCOR^b$, $CO_2R^b$ or $C_{1-3}$alkyl, especially —CH$_2$—, substituted by $OR^a$, $NR^aCOR^b$ or NRSO$_2R^b$, where $R^a$ and $R^b$ are as previously defined.

Where $R^5$ and $R^6$ are taken together there is preferably formed a 5- or 6-membered ring optionally substituted by =O or a hydroxy group, and optionally containing a double bond, which ring optionally contains in the ring an oxygen or sulfur atom or 1 or 2 NH groups, and to which ring is fused a benzene or thiophene ring, which benzene ring is optionally substituted by $OR^a$, where $R^a$ is as previously defined.

As used herein, $OR^a$ is preferably OH or $OCH_3$; $NR^aR^b$ is preferably $NH_2$, $NHCH_3$ $N(CH_3)_2$; $NR^aCOR^b$ is preferably $NHCOCH_3$, $N(CH_3)COCH_3$ $N(Ph)COCH_3$; $NR^aSO_2R^b$ is preferably $NHSO_2CH_3$, $N(CH_3)SO_2CH_3$ or $N(Ph)SO_2CH_3$; and $CO_2R^a$ is preferably $CO_2CH_3$ or $CO_2CH_2CH_3$.

A preferred class of compounds of formula (I) is that wherein Q is $CR^5R^6$, wherein the group $CR^5R^6$ is selected from:

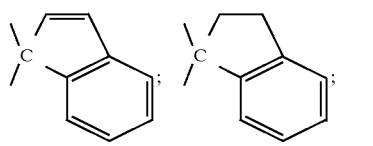

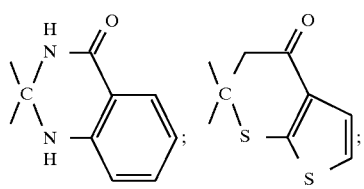

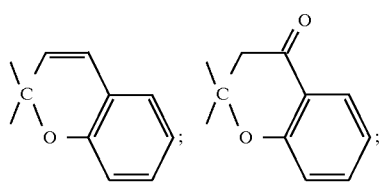

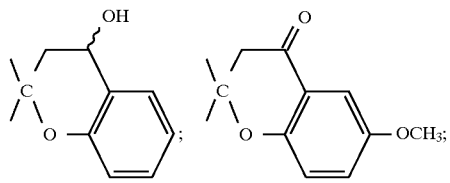

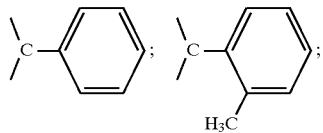

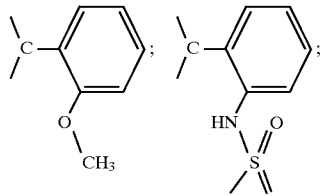

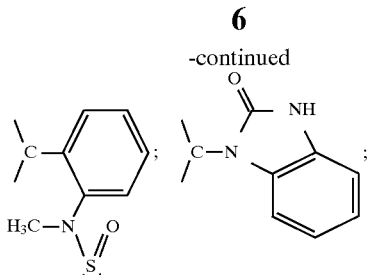

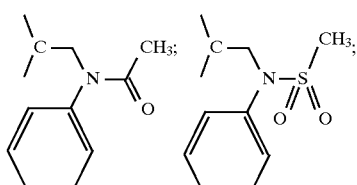

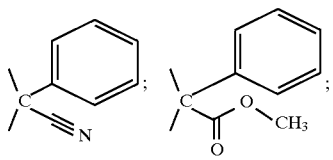

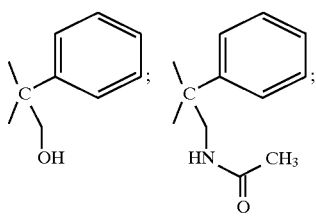

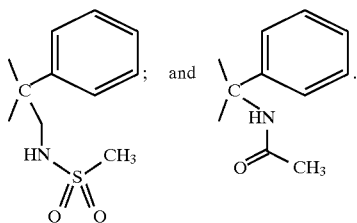

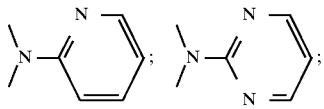

Another preferred class of compounds of formula (I) is that wherein Q is $NR^5$, wherein the group $NR^5$ is selected from:

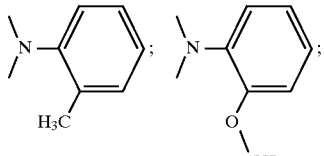

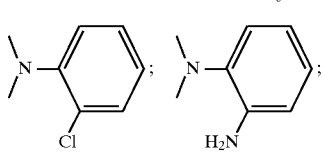

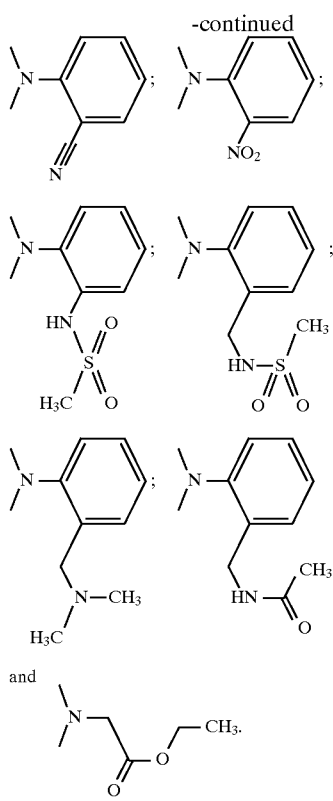

and

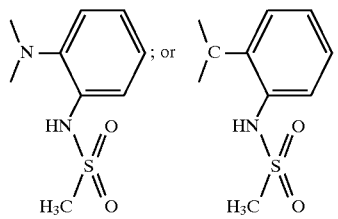

Particularly preferred are those compounds wherein Q represents:

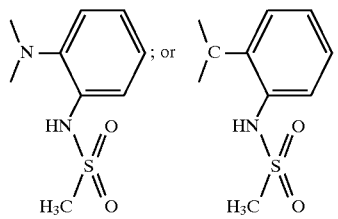

Preferably X and Y are both hydrogen atoms.
Preferably Z is an oxygen atom.

A particular sub-class of compounds according to the invention is represented by compounds of formula (Ia), and pharmaceutically acceptable salts thereof.

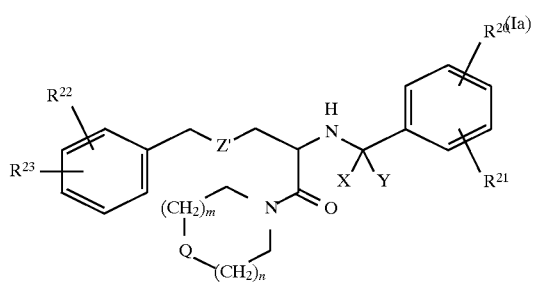

wherein
m, n, Q, X and Y are as defined for formula (I);
Z' is O, S or —CH$_2$—, especially O or S;
R$^{20}$ and R$^{21}$ independently represent hydrogen, C$_{1-6}$alkyl, halogen, trifluoromethyl, OR$^a$, or NR$^a$R$^b$, where R$^a$ and R$^b$ are as previously defined; and R$^{22}$ and R$^{23}$ independently represent hydrogen or halogen, preferably hydrogen or chlorine.

Particular values of R$^{20}$ and R$^{21}$ include hydrogen, chlorine, fluorine, methyl, trifluoromethyl, methoxy and dimethylamino.

Another preferred sub-class of compounds according to the invention is represented by compounds of formula (Ib), and pharmaceutically acceptable salts thereof:

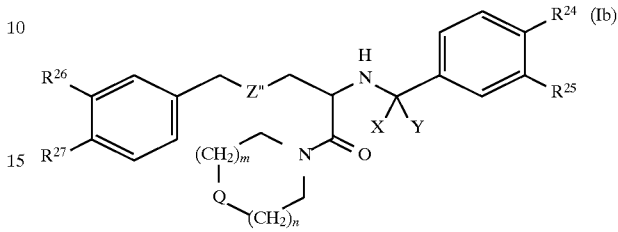

wherein
m, n, Q, X and Y are as defined for formula (I);
Z" is O or —CH$_2$—, especially O;
R$^{24}$ and R$^{25}$ independently represent hydrogen or chlorine; and
R$^{26}$ and R$^{27}$ independently represent hydrogen or chlorine; with the proviso that at least one of R$^{26}$ and R$^{27}$ represents chlorine.

Specific compounds within the scope of the present invention include:
(S)-1-[2-benzylamino-3-(3,4-dichlorobenzyloxy)propionyl]-4-(2-keto-1-benzimidazolinyl)piperidine;
(S)-1'-[3-benzyloxy-2-(3,4-dichlorobenzylamino)propionyl]spiro[1H-indene-1,4'-piperidine];
(S)-N-({1-[3-benzyloxy-2-(3,4-dichlorobenzylamino)propionyl]-4-phenylpiperidin-4-yl}methyl)acetamide;
(S)-1-[3-benzyloxy-2-(3,4-dichlorobenzylamino)propionyl]-4-(methanesulfonamidomethyl)-4-phenylpiperidine;
(S)-1-[3-benzyloxy-2-(3,4-dichlorobenzylamino)propionyl]-4-phenylpiperidine;
(S)-N-{1-[3-benzyloxy-2-(3,4-dichlorobenzylamino)propionyl]-4-phenylpiperidin-4-yl}acetamide;
(S)-1-[2-benzylamino-3-(3,4-dichlorobenzyloxy)propionyl]-4-(2-methoxyphenyl)piperazine;
(S)-1-[2-benzylamino-3-(3,4-dichlorobenzyloxy)propionyl]-4-(2-pyridyl)piperazine;
(S)-1-[2-benzylamino-3-(3,4-dichlorobenzyloxy)propionyl]-4-(2-chlorophenyl)piperazine;
(S)-1-[2-benzylamino-3-(3,4-dichlorobenzyloxy)propionyl]-4-cyano-4-phenylpiperidine;
(S)-methyl 1-[2-benzylamino-3-(3,4-dichlorobenzyloxy)propionyl]-4-phenylpiperidine-4-carboxylate;
(S)-1-[2-benzylamino-3-(3,4-dichlorobenzyloxy)propionyl]-4-(2-methylphenyl)piperazine;
(S)-1-[2-benzylamino-3-(3,4-dichlorobenzyloxy)propionyl]-4-(2-nitrophenyl)piperazine;
(S)-1-[2-benzylamino-3-(3,4-dichlorobenzyloxy)propionyl]-4-(pyrimidin-2-yl)piperazine;
(S)-1-[2-benzylamino-3-(3,4-dichlorobenzyloxy)propionyl]-4-(2-methoxyphenyl)piperidine;
(S)-1-[2-benzylamino-3-(3,4-dichlorobenzyloxy)propionyl]-4-[2-(methanesulfonamido)phenyl]piperidine;
(S)-1-[2-benzylamino-3-(3,4-dichlorobenzyloxy)propionyl]-4-{2-[N-(methyl)methanesulfonamido]phenyl}piperidine;
(S)-1-[-2-benzylamino-3-(3,4-dichlorobenzyloxy)propionyl]-4-(methanesulfonamidomethyl)-4-phenylpiperidine;
(S)-1-[-2-benzylamino-3-(3,4-dichlorobenzyloxy)propionyl]-4-(N-phenylmethanesulfonamidomethyl)piperidine;

(S)-N-({1-[2-benzylamino-3-(3,4-dichlorobenzyloxy) propionyl]-4-phenylpiperidin-4-yl}methyl)acetamide;

(S)-N-({1-[2-benzylamino-3-(3,4-dichlorobenzyloxy) propionyl]piperidin-4-yl}methyl)-N-phenylacetamide;

(S)-1-[2-benzylamino-3-(3,4-dichlorobenzyloxy)propionyl] spiro[piperidine-4,2'(1'H)-quinazolin]-4'(3'H)-one];

(S)-1'-[2-benzylamino-3-(3,4-dichlorobenzyloxy) propionyl]-2,3-dihydrospiro[1H-indene-1,4'-piperidine];

(S)-1-[2-benzylamino-3-(3,4-dichlorobenzyloxy)propionyl]-4-(2-cyanophenyl)piperazine;

(S)-1-[2-benzylamino-3-(3,4-dichlorobenzyloxy)propionyl]-4-(2-methanesulfonamidophenyl)piperazine;

(S)-1-[2-benzylamino-3-(3,4-dichlorobenzyloxy)propionyl] spiro[piperidine-4,6'-[6'H]thieno[2,3-b]thiopyran]-4'(5'H)-one];

(2S, 3'RS)-1'-[2-benzylamino-3-(3,4-dichlorobenzyloxy) propionyl]-spiro[2H-1H-benzopyran-2,3'-piperidine]-4-(3H)-one;

(S)-1'-[2-benzylamino-3-(3,4-dichlorobenzyloxy) propionyl]-6-methoxyspiro[2H-1-benzopyran-2,4'-piperidine]-4-(3H)-one;

(S)-1-[2-benzylamino-3-(3,4-dichlorobenzyloxy)propionyl]-4-(2-methylphenyl)piperidine;

(S)-ethyl 2-{4-[2-benzylamino-3-(3,4-dichlorobenzyloxy) propionyl]piperazin-1-yl}ethanoate;

(S)-1-[2-benzylamino-3-(3,4-dichlorobenzyloxy)propionyl]-4-[2-(methanesulfonamidomethyl)phenyl]piperazine;

(S)-N-(2-{4-[2-benzylamino-3-(3,4-dichlorobenzyloxy) propionyl]piperazin-1-yl}phenylmethyl)acetamide;

(S)-1-[2-benzylamino-3-(3,4-dichlorobenzyloxy)propionyl]-4-[2-(dimethylaminomethyl)phenyl]piperazine;

(S)-1-[2-benzylamino-3-(3,4-dichlorobenzyloxy)propionyl]-4-hydroxymethyl-4-phenylpiperidine;

(S)-1'-[2-benzylamino-3-(3,4-dichlorobenzyloxy) propionyl]spiro[2H-1-benzopyran-2,4'-piperidin]-4-(3H)-one;

(2S, 4'RS)-1'-[2-benzylamino-3-(3,4-dichlorobenzyloxy) propionyl]-3,4-dihydrospiro[2H-1-benzopyran-2,4'-piperidine]-4-ol;

(S)-1'-[2-benzylamino-3-(3,4-dichlorobenzyloxy) propionyl]spiro[2H-1-benzopyran-2,4'-piperidine];

(S)-1-[2-benzylamino-3-(3,4-dichlorobenzyloxy)propionyl]-4-(2-aminophenyl)piperazine;

and pharmaceutically acceptable salts thereof.

For use in medicine, the salts of the compounds of formula (I) will be pharmaceutically acceptable salts. Other salts may, however, be useful in the preparation of the compounds according to the invention (such as the dibenzoyltartrate salts) or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Preferred salts of the compounds according to the invention include the hydrochloride and p-toluenesulphonic acid salts.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

The invention further provides a process for the preparation of a pharmaceutical composition comprising a compound of formula (I), or a salt or prodrug thereof, and a pharmaceutically acceptable carrier, which process comprises bringing a compound of formula (I), or a salt or prodrug thereof into association with a pharmaceutically acceptable carrier.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 μm, particularly 0.1 and 0.5 μm, and have a pH in range of 5.5 to 8.0.

Particularly preferred emulsion compositions are those prepared by mixing a compound of formula (I) with Intralipid™ or the components thereof (soybean oil, egg phospholipids, glycerol and water).

Composition for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, dental pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis; fibrositis, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, and the like; opththalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food and drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances,* Eds. J. Kucharczyk et al, CRC Press Inc., Boca Raton, Fla., U.S.A. (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or GABA$_B$ receptor agonists such as baclofen. Additionally, a compound of formula (I) may be administered in combination with an anti-inflammatory corticosteroid, such as dexamethasone, triamcinolone, triamcinolone acetonide, flunisolide, budesonide, or others such as those disclosed in U.S. Pat. Nos. 2,789,118, 2,990,401, 3,048,581, 3,126,375, 3,929, 768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.,* (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis, headache and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. No. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

It will appreciated that for the treatment or prevention of pain or nociception, a compound of the present invention may be used in conjunction with other analgesics, such as acetaminophen (paracetamol), aspirin and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and 5-$HT_{1A}$ agonists or antagonists, especially 5-$HT_{1A}$ partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-$HT_{1A}$ receptor agonists or antagonists include, in particular, the 5-$HT_{1A}$ receptor partial agonists buspirone, flesinoxan, gepirone and ipsaperone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately by at the discretion of the attendant physician.

According to process (A), compounds of formula (I) wherein X and Y are both hydrogen, may be prepared from compounds of formula (II):

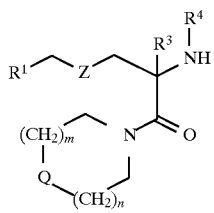

wherein R, $R^1$, $R^3$, $R^4$, $R^5$, Q, Z, m and n are as defined for formula (I), by reaction with an aldehyde of formula $R^2$—CHO in the presence of a reducing agent.

Suitable reducing agent of use in the reaction include hydride reducing agent such as sodium cyanoborohydride or sodium borohydride.

The reaction is conveniently effected in a suitable solvent such as dimethylformamide or dichloromethane, conveniently at room temperature.

According to a process (B), compounds of formula (I) wherein X and Y together form a group =O, may be prepared by the reaction of a compound of formula (II) with an acyl halide of formula $R^2$—COHal where Hal is a halogen atom, typically chlorine, fluorine or bromine, especially chlorine.

The reaction is conveniently effected in the presence of an acylation catalyst such as 4-dimethylaminopyridine in a suitable solvent such as dichloromethane at a temperature between −10° C. and 40° C., conveniently at room temperature.

According to a further process (C), compounds of formula (I) may be prepared by the reaction of a compound of formula (III) with a compound of formula (IV):

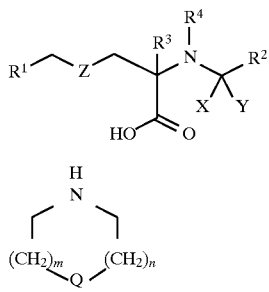

wherein R, $R^1$, $R^2$, $R^3$, $R^4$, $R^5$, Q, X, Y, Z, m and n are as defined for formula (I).

The reaction is effected in the presence of a suitable coupling agent, such as bis(2-oxo-3-oxazolidinyl) phosphinic chloride (BOP-Cl), dicyclocarbonyldiimide, N,N'-carbonyldiimide or 1-(3-dimethylaminopropyl)-3-ethylcarbodiimide optionally in the presence of an additive such as 1-hydroxybenzotriazole.

The choice of solvent for the reaction will depend upon the coupling reagent used thus, for example, with BOP-Cl a suitable solvent is a halogenated hydrocarbon, especially dichloromethane.

Further useful synthetic methods are those commonly used in standard synthesis of amino acids, for example, as described in *Chemistry and Biochemistry of the Amino Acids,* Ed. G. C. Barrett, Chapman and Hall, London 1985.

According to a further process (D), compounds of formula (I) may be prepared by the interconversion of another compound of formula (I).

Interconversion reactions will be readily apparent to a person skilled in the art. Thus, for example, a functional group such as cyano may be modified by reduction, for instance, by catalytic hydrogenation in the presence of a noble metal catalyst or an oxide thereof, e.g. platinum oxide, to give a corresponding compound of formula (I) where the CN group is replaced by —$CH_2NH_2$. This in turn may be modified by reaction with, for example, methanesulfonyl chloride to give a —$CH_2NHSO_2CH_3$ group, or by reaction with acetic anhydride to give a —$CH_2NHCOCH_3$ group.

A carboxylic acid moiety may be esterified in a conventional manner, for example using sulfuric acid and methanol to give the corresponding methyl ester. Compounds where $R^5$ represents —$CH_2N(Ph)SO_2CH_3$ and —$CH_2N(Ph)COCH_3$ may also be prepared from the corresponding compound where $R^5$ is a —$CO_2H$, by reaction with aniline in the presence of BOP-Cl followed by reduction with borane to give an intermediate where $R^5$ is a —$CH_2NH(Ph)$ group which may then be reacted with methanesulfonyl chloride or acetic anhydride to give the desired products.

A nitro group may also be converted to the corresponding sulfonamide by reaction with tin(II) chloride (to give the corresponding primary amine) followed by reaction with methanesulfonyl chloride.

Compounds of formula (II) may be prepared from a suitably protected compound of formula (V):

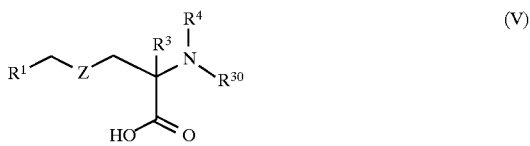

wherein $R^1$, $R^3$, $R^4$, and Z are as defined for formula (I) and $R^{30}$ is an amine protecting group, for example, tert-butoxycarbonyl (t-BOC), by reaction with a compound of formula (IV) using the conditions of process (C), followed by deprotection in a conventional manner, for instance using hydrogen chloride in methanol.

Compounds of formula (III) may be prepared from a deprotected derivative corresponding to a compound of formula (V) by reaction with an aldehyde of formula $R^2$—CHO under the conditions of process (A) or an acyl halide of formula $R^2$—COHal under the conditions of process (B).

Compounds of formula (V) may be prepared by reaction of a compound of formula (VI):

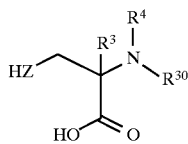

(VI)

wherein $R^3$, $R^4$, and Z are as defined for formula (I) and $R^{30}$ is a protecting group as defined above, by reaction with compound of the formula $R^1$—$CH_2L$, where L is a leaving group, for example, a halogen atom such as chlorine, bromine or iodine, or an alkyl- or arylsulphonyloxy group such as a mesylate or tosylate group. The reaction is effected in the presence of a suitable base, for example, an alkali metal hydride such as sodium hydride.

Compounds of formula (VI) are commercially available or may be prepared by known procedures from available starting materials, for example, using methods described for process (D).

Compounds of formula (VI) where Q is $CR^5R^6$ in which $R^5$ is a phenyl moiety and $R^6$ is hydrogen, may be prepared from a corresponding ketone. Thus, for instance, where m and n are both 1, 1-tert-butoxycarbonylpiperidin-4-one may be converted to the corresponding enol triflate by reaction with lithium diisopropylamide followed by addition of N-phenylbis(trifluoromethanesulfonimide), which in turn may then be coupled to a phenylboronic acid derivative in the presence of a suitable catalyst, for example, tetrakis (triphenylphosphine)palladium(0), followed by hydrogenation in the presence of, for example, palladium on carbon.

Where the above-described processes for the preparation of the compounds according to the invention give rise to mixtures of stereoisomers these isomers may, if desired, be separated, suitably by conventional techniques such as preparative chromatography.

The novel compounds which contain one or more chiral centres may be prepared in racemic form, or individual enantiomers may be prepared either by enantiospecific synthesis or by resolution.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of the invention were tested by the methods set out at pages 82 to 85 of International Patent Specification No. WO 93/04040. The compounds were found to be active with $IC_{50}$ at the $NK_1$ receptor of less than 1 μM.

The compounds of this invention may be formulated as specifically illustrated at pages 81 to 82 of International Patent Specification No. 93/04040.

The following Examples illustrate the preparation of compounds according to the invention.

INTERMEDIATE 1

N-[(4-Phenylpiperidin-4-yl)methyl] methanesulfonamide Hydrochloride a) 4-Aminomethyl-1-t-butoxycarbonyl-4-phenylpiperidine Di-t-butyldicarbonate (13.10 g, 60 mmol) in 1,4-dioxane (50 mL) was added to a stirred mixture of 4-cyano-4-phenylpiperidine hydrochloride (11.14 g, 50 mmol) and sodium carbonate (13.25 g, 125 mmol) in water (150 mL) and the mixture was stirred at room temperature for 6 h. Water (150 mL) was added and the mixture was extracted with ethyl acetate (3×150 mL). The combined organic fractions were washed with aqueous citric acid (10%, 2×100 mL), aqueous sodium hydrogen carbonate (saturated, 100 mL) and brine (100 mL), dried ($MgSO_4$) and the solvent was evaporated under reduced pressure. The residue was dissolved in ethanol-acetic acid (95:5, 200 mL), platinum oxide (1 g) was added and the mixture was shaken under hydrogen (50 psi) for 22 h., adding further platinum oxide (1 g) after 4 h. The mixture was filtered through Hyflo, further ethanol (85 mL), acetic acid (15 mL) and platinum oxide (1 g) were added and the mixture was shaken under hydrogen (50 psi) for 46 h., adding further platinum oxide (1 g) after 22 h. The mixture was filtered through Hyflo and the solvent was evaporated under reduced pressure. Aqueous ammonia (saturated, 200 mL) was added and the mixture was extracted with ethyl acetate (3×200 mL). The combined organic fractions were dried ($MgSO_4$) and the solvent was evaporated under reduced pressure to give the crude title compound as an orange oil (15.92 g), $\delta_H$ (250 MHz, $CDCl_3$) 7.41–7.21 (5H, m), 3.74 (2H, m), 3.05 (2H, m), 2.75 (2H, s), 2.19 (2H, m), 1.80 (2H, br s), 1.69 (2H, m), and 1.43 (9H, s).

b) N-[(1-t-Butoxycarbonyl-4-phenylpiperidin-4-yl) methyl]methanesulfonamide

Methanesulfonyl chloride (2.32 mL, 3.44 g, 33 mmol) was added dropwise to a stirred, cooled (0° C.) solution of crude 4-aminomethyl-1-t-butoxycarbonyl-4-phenylpiperidine (7.96 g) and pyridine (3.64 mL, 3.56 g, 45 mmol) in dichloromethane (100 mL) and the mixture was stirred at room temperature for 18 h. The solvent was evaporated under reduced pressure, aqueous sodium hydrogen carbonate (saturated, 100 mL) was added and the mixture was extracted with ethyl acetate (3×100 mL). The combined organic fractions were washed with aqueous citric acid (10%, 2×100 mL), aqueous sodium hydrogen carbonate (saturated, 100 mL) and brine (100 mL), dried ($MgSO_4$) and the solvent was evaporated under reduced pressure. The residue was purified by flash column chromatography on silica gel, eluting with ethyl acetate/hexane (30:70 increasing to 80:20) to give the title compound as a colorless solid (5.65 g, 61% from 4-cyano-4-phenylpiperidine hydrochloride), $\delta_H$ (250 MHz, $CDCl_3$) 7.46–7.26 (5H, m), 3.88 (1H, br t, J 6.7 Hz), 3.72 (2H, m), 3.23 (2H, br d, J 6.7 Hz), 3.13 (2H, m), 2.71 (3H, s), 2.21 (2H, m), 1.78 (2H, m), and 1.44 (9H, s).

c) N-[(4-Phenylpiperidin-4-yl)methyl] methanesulfonamide Hydrochloride

Methanolic hydrogen chloride (4M, 40 mL) was added to a stirred, cooled (0° C.) suspension of N-[(1-t-butoxycarbonyl-4-phenylpiperidin-4-yl)methyl] methanesulfonamide (5.65 g, 15.4 mmol) in methanol (20 mL) and the mixture was stirred at room temperature for 20 h. The solvent was evaporated under reduced pressure to give the title compound as a tan solid (4.66 g, 100%), $\delta_H$ (250 MHz, $d_6$-DMSO) 9.05 (1H, br s), 8.86 (1H, br s), 7.41–7.26 (5H, m), 6.95 (1H, t, J 6.9 Hz), 3.18 (2H, m), 3.05 (2H, d, J 6.9 Hz), 2.70 (2H, m), 2.64 (3H, s), 2.26 (2H, m), and 2.02 (2H, m).

INTERMEDIATE 2

N-[(4-Phenylpiperidin-4-yl)methyl]acetamide Hydrochloride a) N-[(1-t-Butoxycarbonyl-4-phenylpiperidin-4-yl) methyl]acetamide Acetic anhydride (2.59 mL, 2.81 g, 27.5 mmol) was added dropwise to a stirred, cooled (0° C.) solution of 4-aminomethyl-1-t-butoxycarbonyl-4-phenylpiperidine (7.96 g) and pyridine (3.03 mL, 2.97 g, 37.5 mmol) in dichloromethane (100 mL) and the mixture was stirred at room temperature for 18 h. The solvent was evaporated under reduced pressure, aqueous sodium hydrogen carbonate (saturated, 100 mL) was added and the mixture was extracted with ethyl acetate (3×100 mL). The combined organic fractions were washed with aqueous citric acid (10%, 2×100 mL), aqueous sodium hydrogen carbonate (saturated, 100 mL) and brine (100 mL), dried ($MgSO_4$) and the solvent was evaporated under reduced pressure. The residue was purified by flash column chromatography on silica gel, eluting with ethyl acetate/hexane (50:50 increasing to 100:0) to give the title compound as an off-white solid (5.96 g, 72% from 4-cyano-4-phenylpiperidine hydrochloride), $\delta_H$ (250 MHz, $CDCl_3$) 7.45–7.26 (5H, m), 5.00 (1H, br m), 3.67 (2H, m), 3.45 (2H, br m), 3.21 (2H, m), 2.08 (2H, m), 1.88 (3H, s), 1.78 (2H, m), and 1.43 (9H, s).

b) N-[(4-Phenylpiperidin-4-yl)methyl]acetamide Hydrochloride

Methanolic hydrogen chloride (4M, 40 mL) was added to a stirred, cooled (0° C.) suspension of N-[(1-t-butoxycarbonyl-4-phenylpiperidin-4-yl)methyl] methanesulfonamide (5.90 g, 17.8 mmol) in methanol (40 mL) and the mixture was stirred at room temperature for 20 h. The solvent was evaporated under reduced pressure to give the title compound as a tan foam (4.67 g, 98%), $\delta_H$ (250 MHz, $d_6$-DMSO) 9.09 (1H, br s), 8.88 (1H, br s), 7.73 (1H, t, J 6.3 Hz), 7.43–7.24 (5H, m), 3.18 (4H, m), 2.70 (2H, m), 2.21 (2H, m), 1.97 (2H, m), and 1.76 (3H, s).

INTERMEDIATE 3

Methyl 4-Phenylpiperidine-4-carboxylate Trifluoroacetate a) Methyl 1-t-Butoxycarbonyl-4-phenylpiperidine-4-carboxylate A mixture of 4-phenyl-4-piperidinecarboxylic acid 4-methylbenzenesulfonate (20 g) and methanolic sulfuric acid (10%, 250 mL) was heated under reflux for 24 h., cooled to room temperature and the solvent was evaporated under reduced pressure. The residue was dissolved in water (100 mL) and the pH was adjusted to 8.5 with aqueous sodium hydroxide (4M). 1,4-Dioxan (50 mL) and di-t-butyldicarbonate (11.56 g) were added and the mixture was stirred at room temperature for 24 h. The 1,4-dioxan was evaporated under reduced pressure and the aqueous residue was extracted with ethyl acetate (100 mL). The organic layer was dried ($MgSO_4$) and the solvent was evaporated under reduced pressure to give the title compound as a colorless solid (16.1 g) $\delta_H$ ($CDCl_3$) 1.45 (9H, s), 1.85–1.91 (2H, m), 2.48–2.54 (2H, m), 3.36 (2H, m), 3.73 (3H, s), 3.84–3.95 (2H, m), and 7.22–7.38 (5H, m).

b) Methyl 4-Phenylpiperidine-4-carboxylate Trifluoroacetate

Methyl 1-t-butoxycarbonyl-4-phenylpiperidine-4-carboxylate (5.0 g) was dissolved in trifluoroacetic acid-dichloromethane (10%, 100 mL) and the mixture was stirred at room temperature for 6 h. The solvent was evaporated under reduced pressure to give the title compound as a yellow gum (5.2 g), $\delta_H$ ($CDCl_3$) 2.11–2.20 (2H, m), 2.64–2.68 (2H, m), 3.03–3.13 (2H, m), 3.38–3.44 (2H, m), 3.63 (3H, s), 7.18–7.33 (5H, m), and 7.98 (1H, br s).

INTERMEDIATE 4

4-(2-Methoxyphenyl)piperidine Hydrochloride a) 1-t-Butoxycarbonyl-4-trifluoromethansulfonyloxy-1,2,3,6-tetrahydropyridine A solution of 1-t-butoxycarbonylpiperidin-4-one (1.0 g) in tetrahydrofuran (10 mL) was added dropwise to a stirred, cooled (−78° C.) solution of lithium diisopropylamide [freshly prepared from diisopropylamine (555 mg) and n-butyllithium (1.6M in hexane, 3.5 mL)] in tetrahydrofuran (40 mL) and the mixture was stirred at −78° C. for 20 min. A solution of N-phenylbis(trifluoromethanesulfonimide) (1.96 g) in tetrahydrofuran (10 mL) was added and the solution was allowed to warm to room temperature and stirred for 1 h. The solvent was evaporated under reduced pressure and the residue was partitioned between ethyl acetate and water. The organic layer was dried ($MgSO_4$) and the solvent was evaporated under reduced pressure. The residue was purified by chromatography on alumina (ICN GIII) eluting with EtOAc/Hexane (10:90) to give the title compound as a colorless solid (1.31 g), $\delta_H$ ($CDCl_3$) 1.47 (9H, s), 2.44 (2H, m), 3.63 (2H, t, J 7.0 Hz), 4.04 (2H, m), and 5.76 (1H, br s).

b) 2-Methoxyphenylboronic Acid n-Butyllithium (1.6M in hexane, 13.0 mL) was added to a stirred, cooled (−78° C.) solution of 2-bromoanisole (3.74 g) in tetrahydrofuran (20 mL) and the mixture was stirred at −78° C. for 20 min. Trimethylborate (5.92 g) was added and the solution was allowed to warm to room temperature and stirred for 24 h. The mixture was cooled to 0° C. and acidified with aqueous hydrochloric acid (5M). The mixture was extracted with dichloromethane (4×50 mL) and the combined organic fractions were dried ($MgSO_4$) and the solvent was evaporated under reduced pressure to give the title compound as a colorless solid (3.2 g), $\delta_H$ ($CDCl_3$) 3.91 (3H, s), 6.09 (2H, s), and 6.87–7.03 (4H, m).

c) 4-(2-Methoxyphenyl)piperidine Hydrochloride

Tetrakis(triphenylphosphine)palladium (0) (100 mg) was added to a degassed mixture of 1-t-butoxycarbonyl-4-trifluoromethanesulfonyloxy-1,2,3,6-tetrahydropyridine (810 mg), 2-methoxyphenylboronic acid (519 mg), lithium chloride (405 mg) and aqueous sodium carbonate (2N, 3.5 mL) in 1,2-dimethoxyethane (20 mL). The resulting solution was heated under reflux for 3 h., cooled to room temperature and the solvent was evaporated under reduced pressure. The residue was partitioned between ethyl acetate and aqueous sodium carbonate (2M) and the organic layer was separated, dried ($MgSO_4$) and the solvent was evaporated under reduced pressure. The residue was dissolved in ethanol, palladium on carbon (10%) was added and the mixture was shaken under hydrogen (50 psi.) for 3 h. The mixture was filtered through Hyflo and the solvent was evaporated under reduced pressure. The residue was purified by MPLC on silica gel, eluting with EtOAc/Hexane (5:95) and the residue was deprotected with ethanolic hydrogen chloride to give the title compound as a colorless solid (340 mg), $\delta_H$ ($d_6$-DMSO), 1.54–1.59 (2H, m), 1.77–1.81 (2H, m), 2.77 (2H, td, J 11.0, 1.0 Hz), 3.07 (1H, td, J 11.0, 1.0 Hz), 3.11 (2H, br m), 3.82 (3H, s), 6.85 (1H, d, J 6.0 Hz), 6.93 (1H, t, J 6.0 Hz), 7.15–7.21 (2H, m).

INTERMEDIATE 5

N-[2-(Piperidin-4-yl)phenyl]methanesulfonamide Trifluoroacetate a) t-Butyl (1-t-Butoxycarbonyl-1,2,3,6-tetrahydropyridin-4-yl)phenylcarbamate Tetrakis(triphenylphosphine)palladium (0) (100 mg) was added to a degassed mixture of 1-t-butoxycarbonyl-4-trifluoromethanesulfonyloxy-1,2,3,6-tetrahydropyridine (5.0 g), 2-(t-butoxycarbonylamino)phenylboronic acid (*Tetrahedron Lett.* 1993, 28, 5093) (4.99 g), lithium chloride (1.94 g) and aqueous sodium carbonate (2N, 21 mL) in 1,2-dimethoxyethane (100 mL). The resulting solution was heated under reflux for 3 h., cooled to room temperature and the solvent was evaporated under reduced pressure. The residue was partitioned between ethyl acetate and aqueous sodium carbonate (2M) and the organic layer was separated, dried (MgSO$_4$) and the solvent was evaporated under reduced pressure. The residue was purified by MPLC on silica gel, eluting with EtOAc/Hexane (5:95) to give the title compound as a waxy solid (2.7 g), $\delta_H$ (CDCl$_3$) 1.43 (18H, s), 2.29 (2H, m), 3.57 (2H, t, J 8.0 Hz), 4.00 (2H, m), 5.64 (1H, br s), 6.46 (1H, br s), 6.92–6.96 (2H, m), 7.15–7.19 (1H, m), 7.87 (1H, m).

b) t-Butyl (1-t-Butoxycarbonylpiperidin-4-yl)phenylcarbamate t-Butyl (1-t-butoxycarbonyl-1,2,3,6-tetrahydropyridin-4-yl)phenylcarbamate (2.5 g) was dissolved in ethanol, palladium on carbon (10%) was added and the mixture was shaken under hydrogen (50 psi.) for 3 h. The mixture was filtered through Hyflo and the solvent was evaporated under reduced pressure. The residue was purified by MPLC on silica gel, eluting with EtOAc/Hexane (5:95) to give the title compound as a clear oil (2.44 g), $\delta_H$ (CDCl$_3$) 1.51 (9H, s), 1.55 (9H, s), 1.69 (2H, m), 1.79 (2H, m), 2.77 (3H, m), 4.24 (2H, m), 6.18 (1H, br s), 7.12–7.18 (3H, m), 7.52 (1H, m). m/e (CI$^+$) 377 (MH$^+$).

c) 1-t-Butoxycarbonyl-4-(2-aminophenyl)piperidine t-Butyl (1-t-butoxycarbonylpiperidin-4-yl)phenylcarbamate (290 mg) was dissolved in trifluoroacetic acid-dichloromethane (10%, 20 mL) and stirred at room temperature for 2 h. The solvent was evaporated under reduced pressure and the residue was partitioned between aqueous sodium hydroxide (2M) and ether (30 mL). The organic layer was separated, dried (MgSO$_4$) and the solvent was evaporated under reduced pressure. The residue was dissolved in dichloromethane (20 mL) and cooled in ice. Di-t-butyldicarbonate (161 mg) was added and the mixture was stirred at room temperature for 30 min. The solvent was evaporated under reduced pressure and the residue was purified by MPLC on silica gel, eluting with EtOAc/Hexane (5:95) to give the title compound as a clear oil (141 mg), $\delta_H$ (CDCl$_3$) 1.55 (9H, s), 1.59 (2H, m), 1.82 (2H, m), 2.58 (1H, m), 2.77 (1H, m), 3.64 (2H, br s), 4.16 (2H, m), 6.68–6.79 (2H, m), 7.01–7.26 (2H, m).

d) N-[2-(1-t-Butoxycarbonylpiperidin-4-yl)phenyl]methanesulfonamide

Methanesulfonyl chloride (364 mg) was added to a solution of 1-t-butoxycarbonyl-4-(2-aminophenyl)piperidine (880 mg) and pyridine (252 mg) in dichloromethane. The mixture was heated under reflux for 30 min., cooled to room temperature and the solvent was evaporated under reduced pressure. The residue was partitioned between aqueous citric acid (10%) and ethyl acetate (100 mL). The organic layer was separated, dried (MgSO$_4$) and the solvent was evaporated under reduced pressure to give the title compound as a yellow solid (1.15 g), $\delta_H$ (CDCl$_3$) 1.48 (9H, s), 1.60 (2H, m), 1.73 (2H, m), 2.83 (2H, m), 3.04 (3H, s), 3.09 (1H, m), 4.26 (2H, m), 6.21 (1H, br s), 7.21–7.37 (2H, m). m/e (ES$^+$) 355 (MH$^+$).

f) N-[2-(Piperidin-4-yl)phenyl]methanesulfonamide Trifluoroacetate

N-[2-(1-t-Butoxycarbonylpiperidin-4-yl)phenyl]methanesulfonamide (488 mg) was dissolved in trifluoroacetic acid-dichloromethane (10%, 50 mL) and stirred at room temperature for 2 h. The solvent was evaporated under reduced pressure to give the title compound as a colourless gum (501 mg), $\delta_H$ (CDCl$_3$) 1.97 (4H, br m), 3.03 (3H, s), 3.16 (2H, m), 3.48 (1H, m), 3.68 (2H, m), 7.25–7.43 (4H, m), 8.01 (1H, br s).

INTERMEDIATE 6

N-Methyl-N-[2-(piperidin-4-yl)phenyl]methanesulfonamide Trifluoroacetate a) N-[2-(1-t-Butoxycarbonylpiperidin-4-yl)phenyl]-N-methylmethanesulfonamide Sodium hydride (60% dispersion in mineral oil, 73.4 mg) was added to a solution of N-[2-(1-t-butoxycarbonylpiperidin-4-yl)phenyl]methanesulfonamide (650 mg) in tetrahydrofuran (50 mL) and the mixture was stirred at room temperature for 1 h. Methyl iodide (260 mg) was added and the mixture was stirred at room temperature for 36 h. The solvent was evaporated under reduced pressure, and the residue was partitioned between water and ethyl acetate (100 mL). The organic layer was separated, dried (MgSO$_4$) and the solvent was evaporated under reduced pressure to give the title compound as colorless solid (662 mg), $\delta_H$ (CDCl$_3$) 1.48 (9H, s), 1.73 (2H, m), 1.88 (2H, m), 2.84 (2H, m), 2.97 (3H, s), 3.25 (3H, s), 3.33 (1H, m), 4.13 (2H, m), 7.21–7.36 (4H, m). m/e (ES$^+$) 369 (MH$^+$).

b) N-Methyl-N-[2-(piperidin-4-yl)phenyl]methanesulfonamide Trifluoroacetate

N-[2-(1-t-Butoxycarbonylpiperidin-4-yl)phenyl]-N-methylmethanesulfonamide (662 mg) was dissolved in trifluoroacetic acid-dichloromethane (10%, 50 mL) and stirred at room temperature 2 h. The solvent was evaporated under reduced pressure to give the title compound as a colourless gum (670 mg), m/e (ES$^+$) 269 (MH$^+$).

INTERMEDIATE 7

N-Phenyl-N-[(piperidin-4-yl)methyl]methanesulfonamide Hydrochloride a) 1-t-Butoxycarbonylpiperidine-4-carboxylic Acid Di-t-butyldicarbonate (23.42 g, 107.3 mmol) in dichloromethane (100 mL) was added slowly to a mixture of 4-piperidinecarboxylic acid (12.60 g, 97.6 mmol) and triethylamine (13.60 mL, 9.87 g, 97.6 mmol) in dichloromethane (50 mL) and the mixture was stirred at room temperature for 18 h. N,N-Dimethylethylenediamine (3.46 mL, 2.87 g, 32.5 mmol) was added and the mixture was stirred at room temperature for 30 min. Dichloromethane (100 mL) was added and the mixture was washed with aqueous citric acid (10%, 2×200 mL), dried (MgSO$_4$) and the solvent was evaporated under reduced pressure to give the title compound as a colorless solid (21.05 g, 94%), $\delta_H$ (250 MHz, CDCl$_3$) 4.02 (2H, m), 2.86 (2H, m), 2.49 (1H, m), 1.91 (2H, m), 1.64 (2H, m), and 1.46 (9H, s).

b) N-Phenyl-1-t-butoxycarbonylpiperidine-4-carboxamide

Triethylamine (10.04 mL, 7.28 g, 72 mmol) was added to stirred, cooled (0° C.) mixture of 1-t-butoxycarbonylpiperidine-4-carboxylic acid (6.87 g, 30 mmol), aniline (2.73 mL, 2.79 g, 30 mmol) and bis(2-oxo-3-oxazolidinyl)phosphinic chloride (9.16 g, 36 mmol) in dichloromethane (50 mL) and the mixture was stirred at room temperature for 18 h. The solvent was evaporated under reduced pressure, water (50 mL) was added and the mixture was extracted with ethyl acetate (4×50 mL). The combined organic fractions were washed with aqueous citric acid (10%, 2×50 mL), aqueous sodium hydrogen carbonate (saturated, 2×50 mL) and brine (50 mL), dried (MgSO$_4$) and the solvent was evaporated under reduced pressure. The residue was purified by flash column chromatography on silica gel, eluting with EtOAc/Hexane (40:60) to give the title compound as a colorless foam (7.23 g, 79%), $\delta_H$ (250 MHz, CDCl$_3$) 7.51 (2H, d, J 7.6 Hz), 7.32 (2H, t, J 7.6 Hz), 7.26 (1H, br s), 7.11 (1H, t, J 7.6 Hz), 4.19 (2H, m), 2.78 (2H, m), 2.38 (1H, m), 1.90 (2H, m), 1.77 (2H, m), and 1.47 (9H, s). m/e (ES$^+$) 305 (MH$^+$).

c) N-Phenyl-1-t-butoxycarbonylpiperidine-4-methylamine

Borane-tetrahydrofuran complex (1.0M in tetrahydrofuran, 57 mL, 57 mmol) was added to a stirred, cooled (0° C.) solution N-phenyl-1-t-butoxycarbonylpiperidine-4-carboxamide (5.78 g, 19 mmol) in tetrahydrofuran (95 mL) and the mixture was stirred at room temperature for 18 h. Methanol (10 mL) was added and the solvent was evaporated under reduced pressure. Potassium carbonate (13.13 g, 95 mmol) and methanol (150 mL) were added and the mixture was heated under reflux for 1 h. The mixture was cooled and the solvent was evaporated under reduced pressure. Water (100 mL) was added and the mixture was extracted with dichloromethane (3×100 mL). The combined organic fractions were dried (MgSO$_4$) and the solvent was evaporated under reduced pressure. The residue was purified by flash column chromatography on silica gel, eluting with EtOAc/Hexane (20:80) to give the title compound as a colorless solid (5.08 g, 92%), $\delta_H$ (250 MHz, CDCl$_3$) 7.18 (2H, t, J 7.6 Hz), 6.69 (1H, t, J 7.6 Hz), 6.59 (2H, d, J 7.6 Hz), 4.14 (2H, m), 3.73 (1H, br s), 3.03 (2H, d, J 6.2 Hz), 2.69 (2H, m), 1.79–1.55 (3H, m), 1.46 (9H, s), and 1.20 (2H, m).

d) N-[(1-t-Butoxycarbonylpiperidin-4-yl)methyl]-N-phenylmethanesulfonamide

Methanesulfonyl chloride (0.77 mL, 1.13 g, 9.9 mmol) was added dropwise to a stirred, cooled (0° C.) solution of N-phenyl-1-t-butoxycarbonylpiperidine-4-methylamine (2.61 g, 9 mmol) and pyridine (1.09 mL, 1.07 g, 13.5 mmol) in dichloromethane (50 mL) and the mixture was stirred at room temperature for 16 h. The mixture was cooled in ice and 4-dimethylaminopyridine (220 mg, 1.8 mmol), pyridine (1.09 mL, 1.07 g, 13.5 mmol) and methanesulfonyl chloride (0.77 mL, 1.13 g, 9.9 mmol) were added. The mixture was stirred at room temperature for 24 h. The solvent was evaporated under reduced pressure, aqueous sodium hydrogen carbonate (saturated, 50 mL) was added and the mixture was extracted with ethyl acetate (3×50 mL). The combined organic fractions were washed with aqueous citric acid (10%, 2×50 mL), aqueous sodium hydrogen carbonate (saturated, 50 mL) and brine (50 mL), dried (MgSO$_4$) and the solvent was evaporated under reduced pressure. The residue was recrystallized from ethyl acetate/hexane (2:1, 30 mL) to give the title compound as a colorless solid (2.96 g, 89%), $\delta_H$ (250 MHz, CDCl$_3$) 7.46–7.31 (5H, m), 4.06 (2H, m), 3.56 (2H, d, J 7.2 Hz), 2.85 (3H, s), 2.60 (2H, m), 1.71 (2H, m), 1.57 (1H, m), 1.43 (9H, s), and 1.05 (2H, m).

e) N-Phenyl-N-[(piperidin-4-yl)methyl]methanesulfonamide Hydrochloride

Methanolic hydrogen chloride (4M, 20 mL) was added to a stirred, cooled (0° C.) suspension N-[(1-t-butoxycarbonylpiperidin-4-yl)methyl]-N-phenylmethanesulfonamide (2.84 g, 7.7 mmol) in methanol (10 mL) and the mixture was stirred at room temperature for 1 h. The solvent was evaporated under reduced pressure to give the title compound as a tan foam (2.34 g, 100%), $\delta_H$ (250 MHz, d$_6$-DMSO) 8.90 (2H, br m), 7.45–7.33 (5H, m), 3.53 (2H, d, J 7.0 Hz), 3.19 (2H, m), 2.96 (3H, s), 2.73 (2H, m), 1.80 (2H, m), 1.54 (1H, m), and 1.36 (2H, m).

INTERMEDIATE 8

N-Phenyl-N-[(piperidin-4-yl)methyl]acetamide Hydrochloride a) N-[(1-t-Butoxycarbonylpiperidin-4-yl)methyl]-N-phenylacetamide Acetyl chloride (0.71 mL, 0.79 g, 10.0 mmol) was added dropwise to a stirred, cooled (0° C.) solution of N-phenyl-1-t-butoxycarbonylpiperidine-4-methylamine (2.42 g, 8.3 mmol), pyridine (1.01 mL, 0.99 g, 12.5 mmol) and 4-dimethylaminopyridine (204 mg, 1.7 mmol) in dichloromethane (50 mL) and the mixture was stirred at room temperature for 1 h. Methanol (5 mL) was added and the solvent was evaporated under reduced pressure. Aqueous sodium hydrogen carbonate (saturated, 50 mL) was added and the mixture was extracted with ethyl acetate (3×50 mL). The combined organic fractions were washed with aqueous citric acid (10%, 2×50 mL), aqueous sodium hydrogen carbonate (saturated, 50 mL) and brine (50 mL), dried (MgSO$_4$) and the solvent was evaporated under reduced pressure to give the title compound as a colorless solid (2.73 g, 99%), $\delta_H$ (250 MHz, CDCl$_3$) 7.47–7.15 (5H, m), 4.06 (2H, br m), 3.62 (2H, br m), 2.64 (2H, br m), 1.85 (3H, s), 1.66 (3H, m), 1.44 (9H, s), and 1.20 (2H, m).

b) N-Phenyl-N-[(piperidin-4-yl)methyl]acetamide Hydrochloride

Methanolic hydrogen chloride (4M, 20 mL) was added to a stirred, cooled (0° C.) solution of N-[(1-t-butoxycarbonylpiperidin-4-yl)methyl]-N-phenylacetamide (2.72 g, 8.2 mmol) in methanol (10 mL) and the mixture was stirred at room temperature for 1 h. The solvent was evaporated under reduced pressure to give the title compound as a tan foam (2.17 g, 99%), $\delta_H$ (250 MHz, d$_6$-DMSO) 9.12–8.70 (2H, br m), 7.50–7.33 (5H, m), 3.57 (2H, d, J 7.1 Hz), 3.19 (2H, m), 2.75 (2H, m), 1.73 (6H, m), and 1.37 (2H, m).

INTERMEDIATE 9

Spiro[piperidine-4,2'(1'H)-quinazolin]-4'(3'H)-one] Hydrochloride a) 1-Benzylspiro[piperidine-4,2'(1'H)-quinazolin]-4'(3'H)-one]

Trifluoroacetic acid (50 mL) was added to 2-aminobenzonitrile (6.81 g, 50 mmol) and 1-benzylpiperidin-4-one (10.41 g, 55 mmol) and the mixture was heated under reflux for 8 h. The mixture was cooled and the solvent was evaporated under reduced pressure. Water (300 mL) was added and the pH was adjusted to 10.0 with aqueous sodium hydroxide (4M). The solid was collected and dried in vacuo. Methanol (200 mL) was added and the mixture was heated under reflux for 1 h., cooled and refrigerated. The solid was collected and dried in vacuo. The residue was recrystallized from ethanol-water (80:20, 900 mL) to give the title compound as a colorless solid (7.09 g, 46%), m.p. 224°–246° C. (Dec.), $\delta_H$ (250 MHz, d$_6$-DMSO) 7.98 (1H, s), 7.57 (1H, d, J 7.7 Hz), 7.35–7.20 (6H, m), 6.82 (1H, d, J 7.7 Hz), 6.70 (1H, s), 6.64 (1H, t, J 7.7 Hz), 3.50 (2H, s), 2.49 (4H, m), and 1.78 (4H, m).

b) Spiro[piperidine-4,2'(1'H)-quinazolin]-4'(3'H)-one] Hydrochloride

A suspension of palladium on carbon (10%, 1.8 g) in methanol (30 mL) was added to a solution of 1-benzylspiro [piperidine-4,2'(1'H)-quinazolin]-4'(3'H)-one] (5.53 g, 18 mmol) and formic acid (90%, 9 mL) in degassed methanol (150 mL). The mixture was stirred at room temperature for 72 h., further palladium on carbon (10%, 0.9 g) in methanol (15 mL) and formic acid (90%, 4.5 mL) were added and the mixture was stirred at room temperature for a further 24 h. The mixture was filtered through Hyflo and the solvent was evaporated under reduced pressure. The residue was dissolved in ethanol (90 mL) and ethanolic hydrogen chloride (5M, 4.32 mL) was added. The solvent was evaporated under reduced pressure, propan-2-ol (100 mL) was added and the mixture was heated under reflux for 1 h. The mixture was cooled and refrigerated and the solid was collected and dried in vacuo to give the title compound as a cream solid (3.72 g, 82%), $\delta_H$ (250 MHz, d$_6$-DMSO) 9.28 (1H, br s), 8.88 (1H, br s), 8.37 (1H, s), 7.59 (1H, d, J 7.7 Hz), 7.28 (1H, t, J 7.7 Hz), 7.19 (1H, s), 6.88 (1H, d, J 7.7 Hz), 6.70 (1H, t, J 7.7 Hz), 3.24 (4H, br m), and 1.98 (4H, m). m/e (ES$^+$) 218 (MH$^+$).

INTERMEDIATE 10

N-[2-(Piperazin-1-yl)phenyl]methanesulfonamide a) 1-Benzyl-4-(2-nitrophenyl)piperazine Benzyl bromide (3.1 mL, 26 mmol) was added to a mixture of 1-(2-nitrophenyl)piperazine (4.91 g, 24 mmol) and potassium carbonate (8.2 g, 59 mmol) in dimethylformamide (30 mL) and the mixture was stirred at room temperature for 2 h. The solvent was evaporated under reduced pressure and the residue was azeotroped with xylene. The residue was diluted with ethyl acetate, washed with brine (×3), dried (MgSO$_4$) and the solvent was evaporated under reduced pressure. The residue was purified by flash column chromatography on silica gel, eluting with EtOAc/Hexane (60:40) to give the title compound as an orange oil (4.0 g, 57%). $\delta_H$ (250 MHz, CDCl$_3$) 7.75 (1H, dd, J 1.6, 8.1 Hz), 7.46 (1H, dt, J 1.6, 7.3 Hz), 7.34–7.24 (5H, m), 7.12 (1H, dd, J 7.1, 8.3 Hz), 7.01 (1H, dt, J 1.2, 8.3 Hz), 3.57 (2H, s), 3.10–3.05 (4H, m), and 2.63–2.58 (4H, m).

b) 1-(2-Aminophenyl)-4-benzylpiperazine

Tin (II) chloride (12.77 g, 67 mmol) was added to a solution of 1-benzyl-4-(2-nitrophenyl)piperazine (4.0 g, 13 mmol) in ethanol (50 mL) and the mixture was heated at 70° C. for 1 h. The solvent was evaporated under reduced pressure and the residue was diluted with ethyl acetate and washed with aqueous sodium hydroxide (2M, 4×). The organic layer was dried (MgSO$_4$) and the solvent was evaporated under reduced pressure. The residue was purified by flash column chromatography on silica gel, eluting with EtOAc/Hexane (80:20 increasing to 75:25) to give the title compound as a pale yellow solid (2.61 g, 72%), $\delta_H$ (250 MHz, CDCl$_3$) 7.38–7.25 (5H, m), 7.03–6.89 (2H, m), 6.77–6.70 (2H, m), 4.05–3.90 (2H, br s), 3.59 (2H, s), 2.96–2.92 (4H, m), and 2.65–2.55 (4H, br s).

c) N-[2-(4-Benzylpiperazin-1-yl)phenyl]methanesulfonamide

Methanesulfonyl chloride (0.91 mL, 11.7 mmol) was added to a cooled (0° C.) solution of 1-(2-aminophenyl)-4-benzylpiperazine (2.61 g, 9.8 mmol) and pyridine (0.95 mL, 11.7 mmol) in dichloromethane (30 mL) and the mixture was stirred at room temperature for 16 h. The solvent was evaporated under reduced pressure and triethylamine (1.4 mL) was added. The mixture was azeotroped with xylene, diluted with ethyl acetate and washed with aqueous potassium carbonate (saturated, 3×). The organic layer was dried (MgSO$_4$) and the solvent was evaporated under reduced pressure. The residue was purified by flash column chromatography on silica gel, eluting with CH$_2$Cl$_2$/MeOH (99:1) to give the title compound as yellow oil (2.83 g, 84%). $\delta_H$ (250 MHz, CDCl$_3$) 7.88–7.80 (1H, br s), 7.51 (1H, dd, J 1.6, 8.0 Hz), 7.34–7.27 (5H, m), 7.25 (1H, dd, J 1.6, 7.5 Hz), 7.16 (1H, dt, J 1.6, 7.5 Hz), 7.07 (1H, dt, J 1.7, 7.6 Hz), 3.59 (2H, s), 3.04 (3H, s), 2.90–2.85 (4H, m), and 2.66–2.60 (4H, br s).

d) N-[2-(Piperazin-1-yl)phenyl]methanesulfonamide

A solution of the product of N-[2-(4-benzylpiperazin-1-yl)phenyl]methanesulfonamide (2.83 g, 8.2 mmol) in methanol (40 mL) was purged with nitrogen (0.25 hour). Ammonium formate (1.55 g, 24.6 mmol), formic acid (0.31 mL, 8.21 mmol) and palladium on activated charcoal (0.5 g) were added. The mixture was heated at reflux for 2 h., cooled, filtered, and the solvent was evaporated under reduced pressure. The residue was diluted with ethyl acetate and washed with aqueous potassium carbonate (saturated, 3×). The organic layer was dried (MgSO$_4$) and the solvent was evaporated under reduced pressure to give the title compound as a pale yellow crystalline solid (1.196 g, 57%), $\delta_H$ (250 MHz, CDCl$_3$) 7.52 (1H, dd, J 1.6, 8.0 Hz), 7.23–7.05 (4H, m), 3.06 (3H, s), 3.06–3.02 (4H, m), 2.85–2.78 (4H, m), and 1.80 (1H, br s).

INTERMEDIATE 11

4-[2-Methylphenyl]piperidine Hydrochloride

Tetrakis(triphenylphosphine)palladium (0) (100 mg) was added to a degassed mixture of 1-t-butoxycarbonyl-4-trifluoromethanesulfonyloxy-1,2,3,6-tetrahydropyridine (1.32 g), 2-formylphenylboronic acid (850 mg), lithium chloride (504 mg) and aqueous sodium carbonate (2N, 5.47 mL) in 1,2-dimethoxyethane (30 mL). The resulting solution was heated under reflux for 3 h., cooled to room temperature and the solvent was evaporated under reduced pressure. The residue was partitioned between ethyl acetate and aqueous sodium carbonate (2M) and the organic layer was separated, dried (MgSO$_4$) and the solvent was evaporated under reduced pressure. The residue was dissolved in ethanol, palladium on carbon (10%) was added and the mixture was shaken under hydrogen (50 psi.) for 3 h. The mixture was filtered through Hyflo, the solvent was evaporated under reduced pressure and the residue was purified by MPLC on silica gel, eluting with EtOAc/Hexane (5:95). The residue was dissolved in ethanolic hydrogen chloride (50 mL) and stirred at room temperature for 30 min. The solvent was evaporated under reduced pressure to give the title compound as a colorless solid (610 mg). m/e (ES$^+$) 176 (MH$^+$).

INTERMEDIATE 12

N-[2-(Piperazin-1-yl)phenylmethyl]methanesulfonamide Hydrochloride a) 2-[4-(t-Butoxycarbonyl)piperazin-1-yl]benzonitrile Di-t-butyldicarbonate (2.62 g, 12 mmol) in 1,4-dioxane (8 mL) was added to a mixture of 2-(piperazin-1-yl)

benzonitrile (1.87 g, 10 mmol), sodium carbonate (2.65 g, 25 mmol) and 1,4-dioxane (2 mL) in water (30 mL) and the mixture was stirred at room temperature for 22 h. Water (50 mL) was added and the mixture was extracted with ethyl acetate (3×50 mL). The combined organic fractions were washed with brine (50 mL), dried (MgSO$_4$) and the solvent was evaporated under reduced pressure. The residue was purified by flash column chromatography on silica gel, eluting with CH$_2$Cl$_2$/MeOH/NH$_3$ (Aq.) (99:1:0.1) to give the title compound as a pale yellow oil (2.65 g, 92%), $\delta_H$ (250 MHz, CDCl$_3$) 7.59 (1H, d, J 7.8 Hz), 7.50 (1H, t, J 7.8 Hz), 7.05 (2H, m), 3.64 (4H, t, J 5.0 Hz), 3.15 (4H, t, J5.0 Hz), and 1.49 (9H, s).

b) 2-(4-t-Butoxycarbonylpiperazin-1-yl) phenylmethylamine

Platinum oxide (200 mg) was added to a solution of 2-[4-(t-butoxycarbonyl)piperazin-1-yl]benzonitrile (2.01 g, 7 mmol) in ethanol-acetic acid (95:5, 35 mL) and the mixture was shaken under hydrogen (50 psi) for 22 h, adding further platinum oxide (1 g) after 4 h. The mixture was filtered through Hyflo, further ethanol (85 mL), acetic acid (15 mL) and platinum oxide (1 g) were added and the mixture was shaken under hydrogen (50 psi) for 6 h., adding further platinum oxide (200 mg) after 2 h. and 4 h. The mixture was filtered through Hyflo and the solvent was evaporated under reduced pressure. Water (50 mL) was added, the pH was adjusted to 10.0 with aqueous potassium carbonate (saturated) and the mixture was extracted with ether (3×50 mL). The combined organic fractions were dried (MgSO$_4$) and the solvent was evaporated under reduced pressure to give the crude title compound as a pale yellow oil (2.03 g, 100%), $\delta_H$ (360 MHz, CDCl$_3$) 7.34–7.08 (4H, m), 3.91 (2H, s), 3.57 (4H, t, J 4.9 Hz), 2.87 (4H, t, J 4.9 Hz), 1.60 (2H, br s), and 1.49 (9H, s).

c) N-[2-(4-t-Butoxycarbonylpiperazin-1-yl) phenylmethyl]methanesulfonamide

Methanesulfonyl chloride (0.186 mL, 275 mg, 2.4 mmol) was added dropwise to a stirred, cooled (0° C.) solution of 2-(4-t-butoxycarbonylpiperazin-1-yl)phenylmethylamine (0.58 g, 2 mmol) and pyridine (0.32 mL, 0.32 g, 4 mmol) in dichloromethane (10 mL) and the mixture was stirred at room temperature for 3 h. Further methanesulfonyl chloride (0.046 mL, 69 mg, 0.6 mmol) was added and the mixture was stirred at room temperature for 3 h. Water (1 mL) was added and the solvent was evaporated under reduced pressure. Aqueous sodium hydrogen carbonate (saturated, 20 mL) and water were added and the mixture was extracted with ethyl acetate (3×20 mL). The combined organic fractions were washed with aqueous citric acid (10%, 2×20 mL), aqueous sodium hydrogen carbonate (saturated, 2×20 mL) and brine (20 mL), dried (MgSO$_4$) and the solvent was evaporated under reduced pressure. The residue was purified by MPLC on silica gel, eluting with CH$_2$Cl$_2$/MeOH/NH$_3$ (Aq.) (99:1:0.1) to give the title compound as a colorless solid (344 mg, 47%), $\delta_H$ (250 MHz, CDCl$_3$) 7.33 (2H, m), 7.15 (2H, m), 5.80 (1H, br t, J 4.0 Hz), 4.40 (2H, d, J 4.0 Hz), 3.60 (4H, br t, J 3.4 Hz), 2.88 (4H, t, J 3.4 Hz), 2.82 (3H, s), and 1.49 (9H, s). m/e (ES$^+$) 370 (MH$^+$).

d) N-[2-(Piperazin-1-yl)phenylmethyl] methanesulfonamide Hydrochloride

Methanolic hydrogen chloride (4M, 2.5 mL) was added to a stirred, cooled (0° C.) suspension of N-[2-(4-t-butoxycarbonylpiperazin-1-yl)phenylmethyl] methanesulfonamide (330 mg, 0.89 mmol) in methanol (1 mL) and the mixture was stirred at room temperature for 4 h. The solvent was evaporated under reduced pressure to give the title compound as an off-white solid (269 mg, 99%), $\delta_H$ (360 MHz, d$_6$-DMSO) 9.15 (2H, br s), 7.44 (1H, d, J 7.6 Hz), 7.42 (1H, br t, J 5.6 Hz), 7.31 (1H, t, J 7.6 Hz), 7.16 (2H, m), 4.22 (2H, d, J 5.6 Hz), 3.23 (4H, m), 3.06 (4H, m), and 2.92 (3H, s). m/e (ES$^+$) 270 (MH$^+$).

INTERMEDIATE 13

N-[2-(Piperazin-1-yl)phenylmethyl]acetamide Hydrochloride a) N-[2-(4-t-Butoxycarbonylpiperazin-1-yl) phenylmethyl]acetamide Acetic anhydride (0.40 mL, 0.43 g, 4.2 mmol) was added to a stirred, cooled (0° C.) solution of 2-(4-t-butoxycarbonylpiperazin-1-yl)phenylmethylamine (1.02 g, 3.5 mmol), 4-dimethylaminopyridine (86 mg, 0.7 mmol) and pyridine (0.57 mL, 0.55 g, 7 mmol) in dichloromethane (10 mL) and the mixture was stirred at room temperature for 1 h. Methanol (1 mL) was added and the mixture was stirred at room temperature for 2 h. Aqueous sodium hydrogen carbonate (saturated, 20 mL) and water (10 mL) were added and the mixture was extracted with dichloromethane (3×20 mL). The combined organic fractions were dried (MgSO$_4$) and the solvent was evaporated under reduced pressure. The residue was purified by MPLC on silica gel, eluting with CH$_2$Cl$_2$/MeOH/NH$_3$ (Aq.) (99.5:0.5:0.05 increasing to 98:2:0.2) to give the title compound as a colorless solid (681 mg, 58%), $\delta_H$ (250 MHz, CDCl$_3$) 7.28 (2H, m), 7.12 (2H, m), 6.26 (1H, br s), 4.55 (2H, d, J 5.6 Hz), 3.57 (4H, t, J 4.9 Hz), 2.86 (4H, t, J 4.9 Hz), 2.03 (3H, s), and 1.49 (9H, s). m/e (ES$^+$) 334 (MH$^+$).

b) N-[2-(Piperazin-1-yl)phenylmethyl]acetamide Hydrochloride

Methanolic hydrogen chloride (4M, 5 mL) was added to a stirred, cooled (0° C.) suspension of N-[2-(4-t-butoxycarbonylpiperazin-1-yl)phenylmethyl]acetamide (668 mg, 2 mmol) in methanol (2 mL) and the mixture was stirred at room temperature for 4 h. The solvent was evaporated under reduced pressure to give the title compound as a colorless foam (536 mg, 99%), $\delta_H$ (360 MHz, d$_6$-DMSO) 9.20 (2H, br s), 8.26 (1H, br t, J 5.8 Hz), 7.26 (2H, m), 7.12 (2H, m), 4.33 (2H, d, J 5.8 Hz), 3.22 (4H, m), 3.04 (4H, m), and 1.89 (3H, s). m/e (ES$^+$) 234 (MH$^+$).

INTERMEDIATE 14

N,N-Dimethyl-[2-(piperazin-1-yl)phenyl] methylamine Dihydrochloride a) N,N-Dimethyl-2-(4-t-butoxycarbonylpiperazin-1-yl) phenylmethylamine Sodium cyanoborohydride (1.10 g, 17.5 mmol) was added to a stirred, cooled (0° C.) mixture of 2-(4-t-butoxycarbonylpiperazin-1-yl)phenylmethylamine (1.02 g, 3.5 mmol) and aqueous formaldehyde (37%, 1.31 mL, 1.42 g, 17.5 mmol) in acetonitrile (10 mL) and the mixture was stirred at room temperature for 18 h. The solvent was evaporated under reduced pressure, aqueous sodium hydrogen carbonate (saturated, 20 mL) and water (10 mL) were added and the mixture was extracted with ethyl acetate (3×20 mL). The combined organic fractions were washed with aqueous sodium hydrogen carbonate (saturated, 3×20 mL) and brine (20 mL), dried (MgSO$_4$) and the solvent was evaporated under reduced pressure. The residue was purified by MPLC on silica gel, eluting with CH$_2$Cl$_2$/MeOH/NH$_3$ (Aq.) (99:1:0.1 increasing to 96:4:0.4) to give the title compound as a colorless oil (400 mg, 36%), $\delta_H$ (250 MHz, CDCl$_3$) 7.40 (1H, d, J 7.5 Hz), 7.25 (1H, t, J 7.5 Hz), 7.08 (2H, m), 3.56 (4H, t, J 5.0 Hz), 3.52 (2H, s), 2.91 (4H, t, J 5.0 Hz), 2.27 (6H, s), and 1.49 (9H, s). m/e (ES$^+$) 320 (MH$^+$)

b) N,N-Dimethyl-[2-(piperazin-1-yl)phenyl]methylamine Dihydrochloride

Methanolic hydrogen chloride (4M, 2.5 mL) was added to a stirred, cooled (0° C.) solution of N,N-dimethyl-2-(4-t-butoxycarbonylpiperazin-1-yl)phenylmethylamine (392 mg, 1.2 mmol) in methanol (1 mL) and the mixture was stirred at room temperature for 4 h. The solvent was evaporated under reduced pressure to give the title compound as a colorless solid (350 mg, 100%), $\delta_H$ (360 MHz, d$_6$-DMSO) 9.92 (1H, br s), 9.26 (2H, br s), 7.62 (1H, d, J 7.7 Hz), 7.49 (1H, t, J 7.7 Hz), 7.31 (2H, m), 4.30 (2H, d, J 5.5 Hz), 3.31 (4H, m), 3.04 (4H, m), 2.73 (3H, s), and 2.72 (3H, s). m/e (ES$^+$) 220 (MH$^+$).

EXAMPLE 1

(S)-1-[2-Benzylamino-3-(3,4-dichlorobenzyloxy) propionyl]-4-(2-keto-1-benzimidazolinyl)piperidine Hydrochloride a) (S)-1-[2-t-Butoxycarbonylamino-3-(3,4-dichlorobenzyloxy)propionyl]-4-(2-keto-1-benzimidazolinyl)piperidine Triethylamine (0.28 mL, 0.20 g, 2 mmol) was added to a stirred, cooled (0° C.) mixture of (S)-2-t-butoxycarbonylamino-3-(3,4-dichlorobenzyloxy)propionic acid (prepared according to the method of Sugano. H, and Miyoshi. M, *J. Org. Chem* 1976, 41, 2352) (364 mg, 1 mmol), 4-(2-keto-1-benzimidazolinyl)piperidine (217 mg, 1 mmol) and bis(2-oxo-3-oxazolidinyl)phosphinic chloride (305 mg, 2 mmol) in dichloromethane (10 mL) and the mixture was stirred at room temperature for 1h. Aqueous sodium hydrogen carbonate (saturated, 40 mL) and water (10 mL) were added and the mixture was extracted with dichloromethane (3×50 mL). The combined organic fractions were washed with aqueous citric acid (10%, 2×50 mL), aqueous sodium hydrogen carbonate (saturated, 2×50 mL) and brine (50 mL), dried (MgSO$_4$) and the solvent was evaporated under reduced pressure. The residue was purified by flash column chromatography on silica gel, eluting with CH$_2$Cl$_2$/MeOH (99:1) to give the title compound as a colorless foam (318 mg, 56%). m/e (ES$^+$) 563 (MH$^+$).

b) (S)-1-[2-Benzylamino-3-(3,4-dichlorobenzyloxy) propionyl]-4-(2-keto-1-benzimidazolinyl)piperidine Hydrochloride Methanolic hydrogen chloride (4M, 2 mL) was added to a solution of (S)-1-[2-t-butoxycarbonylamino-3-(3,4-dichlorobenzyloxy)propionyl]-4-(2-keto-1-benzimidazolinyl)piperidine (298 mg, 0.53 mmol) in methanol (2 mL) and the mixture was stirred at room temperature for 5 h. The solvent was evaporated under reduced pressure, dichloromethane (5 mL), triethylamine (0.148 mL, 107 mg, 1.06 mmol), benzaldehyde (0.065 mL, 67 mg, 0.64 mmol) and magnesium sulfate (300 mg) were added. The mixture was stirred at room temperature for 4 h., filtered and the solvent was evaporated under reduced pressure. Methanol (5 mL) was added, the mixture was cooled to 0° C. and sodium borohydride (40 mg, 1.06 mmol) was added. The mixture was stirred at room temperature for 1 h., aqueous sodium hydrogen carbonate (saturated, 20 mL) and water (10 mL) were added and the mixture was extracted with dichloromethane (3×20 mL). The combined organic fractions were dried (MgSO$_4$) and the solvent was evaporated under reduced pressure. The residue was purified by flash column chromatography on silica gel, eluting with CH$_2$Cl$_2$/MeOH/ NH$_3$ (Aq.) (99:1:0.1 increasing to 95:5:0.5). The residue was dissolved in methanol (5 mL), cooled to 0° C. and methanolic hydrogen chloride (1M, 0.44 mL) was added. The solvent was evaporated under reduced pressure and the residue was triturated with ether (5 mL). The solid was collected and dried in vacuo to give the title compound as a colorless solid (212 mg, 68%), m.p. 148°–151° C. Found: C, 57.18; H, 5.29; N, 9.27. C$_{29}$H$_{30}$Cl$_2$N$_4$O$_3$.HCl.H$_2$O requires: C, 57.29; H, 5.47; N, 9.22%. m/e (ES$^+$) 553 (MH$^+$).

The following compounds were prepared from (S)-2-t-butoxycarbonylamino-3-benzyloxypropionic acid or (S)-2-t-butoxycarbonylamino-3-(3,4-dichlorobenzyloxy) propionic acid (prepared according to the method of Sugano. H, and Miyoshi. M, *J. Org. Chem* 1976, 41, 2352) and the appropriate substituted piperidine or piperazine, followed by reductive amination with benzaldehyde or 3,4-dichlorobenzaldehyde, according to the method of Example 1:

References:

N-(4-Phenylpiperidin-4-yl)acetamide (EP512901A1)

Spiro[1H-indene-1,4'-piperidine]Hydrochloride (*J. Med. Chem.* 1992, 35, 2033–2039)

2,3-Dihydrospiro[1H-indene-1,4'-piperidine]Hydrochloride (*J. Med. Chem.* 1992, 35, 2033–2039)

Spiro[piperidine-4,6'-[6'H]thieno[2,3-b]thiopyran]-4'(5'H)-one]Hydrochloride (U.S. Pat. No. 5,206,240, Example 2A)

(RS)-Spiro[2H-1-benzopyran-2,3'-piperidine]-4-(3H)-one Hydrochloride (U.S. Pat. No. 5,206,240, Example 52B)

6-methoxyspiro[2H-1-benzopyran-2,4'-piperidine]-4-(3H)-one Hydrochloride (U.S. Pat. No. 5,206,240, Example 231)

Spiro[2H-1-benzopyran-2,4'-piperidine]-4-(3H)-one Hydrochloride (U.S. Pat. No. 5,206,240, Example 67A)

EXAMPLE 2

(S)-1'-[3-Benzyloxy-2-(3,4-dichlorobenzylamino) propionyl]spiro[1H-indene-1,4'-piperidine] Hydrochloride Found C, 62.51; H, 560; N, 4.95. C$_{30}$H$_{30}$Cl$_2$N$_2$O$_2$.HCl.H$_2$O requires: C, 62.56; H, 5.77; N, 4.86%. m/e (CI$^+$) 521 (MH$^+$).

EXAMPLE 3

(S)-N-({1-[3-Benzyloxy-2-(3,4-dichlorobenzylamino)propionyl]-4-phenylpiperidin-4-yl}methyl)acetamide Hydrochloride Found C, 57.90; H, 6.11; N, 6.54. C$_{31}$H$_{35}$Cl$_2$N$_3$O$_3$.HCl.2H$_2$O requires: C, 58.08; H, 6.23; N, 6.55%. m/e (CI$^+$) 568 (MH$^+$).

EXAMPLE 4

(S)-1-[3-Benzyloxy-2-(3,4-dichlorobenzylamino) propionyl]-4-(methanesulfonamidomethyl)-4-phenylpiperidine Hydrochloride Found C, 55.20; H, 5.97; N, 6.99. C$_{30}$H$_{35}$Cl$_2$N$_3$O$_4$S.HCl.0.5H$_2$O requires: C, 55.43; H, 5.74; N, 6.46%. m/e (CI$^+$) 604 (MH$^+$).

EXAMPLE 5

(S)-1-[3-Benzyloxy-2-(3,4-dichlorobenzylamino) propionyl]-4-phenylpiperidine Hydrochloride Found C, 62.95; H, 5.69; N, 4.74. C$_{28}$H$_{30}$Cl$_2$N$_2$O$_2$.HCl requires: C, 62.99; H, 5.85; N, 5.25%. m/e (CI$^+$) 497 (MH$^+$).

EXAMPLE 6

(S)-N-{1-[3-Benzyloxy-2-(3,4-dichlorobenzylamino)propionyl]-4-phenylpiperidin-4-yl}acetamide Hydrochloride Found C, 59.74; H, 5.70; N, 6.49. $C_{30}H_{33}Cl_2N_3O_3 \cdot HCl \cdot 0.75H_2O$ requires: C, 59.60; H, 5.91; N, 6.95%. m/e (CI$^+$) 554 (MH$^+$).

EXAMPLE 7

(S)-1-[2-Benzylamino-3-(3,4-dichlorobenzyloxy)propionyl]-4-(2-methoxyphenyl)piperazine Hydrochloride Found C, 57.90; H, 5.64; N, 7.09. $C_{28}H_{31}Cl_2N_3O_3 \cdot HCl \cdot H_2O$ requires: C, 57.69; H, 5.88; N, 7.20%. m/e (ES$^+$) 528 (MH$^+$).

EXAMPLE 8

(S)-1-[2-Benzylamino-3-(3,4-dichlorobenzyloxy)propionyl]-4-(2-pyridyl)piperazine Hydrochloride $\delta_H$ (d$_6$-DMSO) 3.6–3.9 (8H, br m), 3.84 (2H, d, J 4.0 Hz), 4.13 (2H br m), 4.54 (2H, d, J 4.0 Hz), 4.73 (1H, br s), 6.90 (1H, br s), 7.30 (1H, br m), 7.32 (1H, m), 7.40 (2H, m), 7.51 (2H, m), 7.6 (2H, m), 7.73 (1H br m), 8.09 (1H, m). m/e (ES$^+$) 499 (MH$^+$).

EXAMPLE 9

(S)-1-[2-Benzylamino-3-(3,4-dichlorobenzyloxy)propionyl]-4-(2-chlorophenyl)piperazine Hydrochloride Found C, 56.70; H, 4.99; N, 7.10. $C_{27}H_{28}Cl_3N_3O_2 \cdot HCl$ requires: C, 56.96; H, 5.13; N, 7.38%. m/e (ES$^+$) 532 (MH$^+$).

EXAMPLE 10

(S)-1-[2-Benzylamino-3-(3,4-dichlorobenzyloxy)propionyl]-4-cyano-4-phenylpiperidine Hydrochloride M.p. 219°–222° C. Found: C, 61.91; H, 5.22; N, 7.55. $C_{29}H_{29}Cl_2N_3O_2 \cdot HCl \cdot 0.25H_2O$ requires: C, 61.82; H, 5.46; N, 7.46%. m/e (ES$^+$) 522 (MH$^+$).

EXAMPLE 11

(S)-Methyl 1-[2-Benzylamino-3-(3,4-dichlorobenzyloxy)propionyl]-4-phenylpiperidine-4-carboxylate $\delta_H$ (CDCl$_3$) 1.20–2.0 (4H, m), 2.36–2.58 (2H, m), 2.81–3.17 (2H m), 3.45–3.62 (2H, m), 3.67 (3H, s), 3.68–3.79) (2H, m), 4.29 (2H, d, J 6.0 Hz), 4.70 (1H, m), 6.90 (1H, br s), 6.96–7.41 (12H, m). m/e (ES$^+$) 555 (MH$^+$).

EXAMPLE 12

(S)-1-[2-Benzylamino-3-(3,4-dichlorobenzyloxy)propionyl]-4-(2-methylphenyl)piperazine Dihydrochloride Found: C, 55.30; H, 5.71; N, 6.91. $C_{28}H_{31}Cl_2N_3O_2 \cdot 2HCl \cdot H_2O$ requires: C, 55.73; H, 5.85; N, 6.96%. m/e (ES$^+$) 512 (MH$^+$).

EXAMPLE 13

(S)-1-[2-Benzylamino-3-(3,4-dichlorobenzyloxy)propionyl]-4-(2-nitrophenyl)piperazine Sesquihydrochloride Found: C, 52.62; H, 5.15; N, 8.96. $C_{27}H_{28}Cl_2N_4O_4 \cdot 1.5HCl \cdot H_2O$ requires: C, 52.63; H, 5.15; N, 9.09%. m/e (ES$^+$) 543 (MH$^+$).

EXAMPLE 14

(S)-1-[2-Benzylamino-3-(3,4-dichlorobenzyloxy)propionyl]-4-(pyrimidin-2-yl)piperazine Dihydrochloride Found: C, 50.08; H, 5.21; N, 11.42. $C_{25}H_{27}Cl_2N_5O_2 \cdot 2HCl \cdot 1.5H_2O$ requires: C, 50.02; H, 5.37; N, 11.66%. m/e (ES$^+$) 500 (MH$^+$).

EXAMPLE 15

(S)-1-[2-Benzylamino-3-(3,4-dichlorobenzyloxy)propionyl]-4-(2-methoxyphenyl)piperidine Hydrochloride $\delta_H$ (d$_6$-DMSO) 1.08–1.12 (2H, m), 1.64 (1H, m), 1.76 (1H m), 2.66–2.69 (1H, m), 3.02—3.10 (2H, br m), 3.33 (3H, s) 3.77 (2H, d, J 11.0 Hz), 3.84–3.87 (3H, m), 4.12–4.20 (2H, m), 4.48–4.62 (3H, m) 6.82 (1H, m), 6.97 (1H, m), 7.00 (1H, m), 7.22 (1H, m), 7.34 (3H, m), 7.51 (2H m), 7.67 (2H m). m/e (ES$^+$) 527 (MH$^+$).

EXAMPLE 16

(S)-1-[2-Benzylamino-3-(3,4-dichlorobenzyloxy)propionyl]-4-[2-(methanesulfonamido)phenyl]piperidine Hydrochloride $\delta_H$ (d$_6$-DMSO) 1.19–1.23 (2H, m), 1.76 (1H, m), 2.51–2.70 (1H m), 2.99 (3H, s), 3.04–3.10 (2H, m), 3.89 (3H, m), 4.13–4.21 (2H, m), 4.50 (2H, s), 4.52–4.61 (2H, m), 6.89 (1H, br s), 7.20–7.68 (12H, m). m/e (ES$^+$) 590 (MH$^+$).

EXAMPLE 17

(S)-1-[2-Benzylamino-3-(3,4-dichlorobenzyloxy)propionyl]-4-{2-[N-(methyl)methanesulfonamido]phenyl}piperidine Hydrochloride $\delta_H$ (d$_6$-DMSO) 1.22–1.77 (4H, m), 2.71 (2H, m), 3.03 (3H, s), 3.16 (3H, s), 3.87 (3H, m), 4.11 (2H, m), 4.17 (1H, m), 4.49–4.60 (4H, m), 7.25–7.69 (12H, m). m/e (ES$^+$) 604 (MH$^+$).

EXAMPLE 18

(S)-1-[2-Benzylamino-3-(3,4-dichlorobenzyloxy)propionyl]-4-(methanesulfonamidomethyl)-4-phenylpiperidine Hydrochloride M.p. 165°–167° C. Found: C, 55.43; H, 5.46; N, 6.34. $C_{30}H_{35}Cl_2N_3O_4S \cdot HCl \cdot 0.5H_2O$ requires: C, 55.43; H, 5.74; N, 6.46%. m/e (ES$^+$) 604 (MH$^+$).

EXAMPLE 19

(S)-1-[2-Benzylamino-3-(3,4-dichlorobenzyloxy)propionyl]-4-(N-phenylmethanesulfonamidomethyl)piperidine Hydrochloride M.p. 190°–192° C. Found: C, 55.11; H, 5.86; N, 6.42. $C_{30}H_{35}Cl_2N_3O_4S \cdot HCl \cdot 0.5H_2O$ requires: C, 55.43; H, 5.74; N, 6.46%. m/e (ES$^+$) 604 (MH$^+$).

EXAMPLE 20

(S)-N-({1-[2-Benzylamino-3-(3,4-dichlorobenzyloxy)propionyl]-4-phenylpiperidin-4-yl}methyl)acetamide Hydrochloride M.p. 165°–167° C. Found: C, 61.10; H, 6.19; N, 6.72. $C_{31}H_{35}Cl_2N_3O_3 \cdot HCl \cdot 0.25H_2O$ requires: C, 61.09; H, 6.04; N, 6.89%. m/e (ES$^+$) 568 (MH$^+$).

EXAMPLE 21

(S)-N-({1-[2-Benzylamino-3-(3,4-dichlorobenzyloxy)propionyl]piperidin-4-yl}methyl)-N-phenylacetamide Hydrochloride M.p. 108°–110° C. Found: C, 61.17; H, 5.97; N, 6.91. $C_{31}H_{35}Cl_2N_3O_3$.HCl requires: C, 61.54; H, 6.00; N, 6.95%. m/e (ES$^+$) 568 (MH$^+$).

EXAMPLE 22

(S)-1-[2-Benzylamino-3-(3,4-dichlorobenzyloxy)propionyl]spiro[piperidine-4,2'(1'H)-quinazolin]-4'(3'H)-one]Hydrochloride M.p. 145°–147° C. Found: C, 57.95; H, 5.26; N, 8.94. $C_{29}H_{30}Cl_2N_4O_3$.HCl.0.6H$_2$O requires: C, 57.98; H, 5.40; N, 9.33%. m/e (ES$^+$) 553 (MH$^+$).

EXAMPLE 23

(S)-1'-[2-Benzylamino-3-(3,4-dichlorobenzyloxy)propionyl]-2,3-dihydrospiro[1H-indene-1,4'-piperidine]Hydrochloride M.p. 207°–209° C. Found: C, 64.30; H, 5.72; N, 5.04. $C_{30}H_{32}Cl_2N_2O_2$.HCl requires: C, 64.35; H, 5.94; N, 5.00%. m/e (ES$^+$) 523 (MH$^+$).

EXAMPLE 24

(S)-1-[2-Benzylamino-3-(3,4-dichlorobenzyloxy)propionyl]-4-(2-cyanophenyl)piperazine Sesquihydrochloride Found: C, 58.58; H, 4.97; N, 9.78. $C_{28}H_{28}Cl_2N_4O_2$.1.5 HCl requires: C, 58.17; H, 5.14; N, 9.69%. m/e (ES$^+$) 523 MH$^+$).

EXAMPLE 25

(S)-1-[2-Benzylamino-3-(3,4-dichlorobenzyloxy)propionyl]-4-(2-methanesulfonamidophenyl)piperazine Dihydrochloride Found: C, 50.49; H, 5.20; N, 8.19. $C_{28}H_{32}Cl_2N_4O_4S$.2HCl requires: C, 50.61; H, 5.16; N, 8.43%. m/e (ES$^+$) 591 (MH$^+$).

EXAMPLE 26

(S)-1-[2-Benzylamino-3-(3,4-dichlorobenzyloxy)propionyl]spiro[piperidine-4,6'-[6'H]thieno[2,3-b]thiopyran]-4'(5'H)-one]Hydrochloride M.p. 172°–174° C. Found: C, 54.54; H, 4.58; N, 4.36. $C_{28}H_{28}Cl_2N_2O_3S_2$.HCl.0.25H$_2$O requires: C, 54.55; H, 4.82; N, 4.54%. m/e (ES$^+$) 575 (MH$^+$).

EXAMPLE 27

(2S, 3'RS)-1'-[2-Benzylamino-3-(3,4-dichlorobenzyloxy)propionyl]spiro[2H-1-benzopyran-2,3'-piperidine]-4-(3H)-one Hydrochloride M.p. 99°–101° C. Found: C, 60.33; H, 5.15; N, 4.40. $C_{30}H_{30}Cl_2N_2O_4$.HCl.0.5H$_2$O requires: C, 60.16; H, 5.39; N, 4.68%. m/e (ES$^+$) 553 (MH$^+$).

EXAMPLE 28

(S)-1'-[2-Benzylamino-3-(3,4-dichlorobenzyloxy)propionyl]-6-methoxyspiro[2H-1-benzopyran-2,4'-piperidin]-4-(3H)-one Hydrochloride M.p. 184°–186° C. Found: C, 59.68; H, 5.46; N, 4.44. $C_{31}H_{32}Cl_2N_2O_5$.HCl requires: C, 60.06; H, 5.37; N, 4.52%. m/e (ES$^+$) 583 (MH$^+$).

EXAMPLE 29

(S)-1-[2-Benzylamino-3-(3,4-dichlorobenzyloxy)propionyl]-4-(2-methylphenyl)piperidine $\delta_H$ (CDCl$_3$) 1.49–1.67 (4H, m), 2.32 (3H, s), 2.65 (1H, m), 2.93 (2H, m), 3.52–2.70 (2H, m), 3.79–3.70 (2H, m), 4.44 (2H, s), 4.70 (2H, s), 4.83 (1H, m), 7.11–7.47 (12H, m). m/e (ES$^+$) 511 (MH$^+$).

EXAMPLE 30

(S)-Ethyl-2-{4-[2-Benzylamino-3-(3,4-dichlorobenzyloxy)propionyl]piperazin-1-yl}ethanoate Dihydrochloride M.p. 208°–210° C. Found: C, 51.40; H, 5.92; N, 7.15. $C_{25}H_{31}Cl_2N_3O_4$.2HCl requires: C, 51.65; H, 5.72; N, 7.23%. m/e (ES$^+$) 508 (MH$^+$).

EXAMPLE 31

(S)-1-[2-Benzylamino-3-(3,4-dichlorobenzyloxy)propionyl]-4-[2-(methanesulfonamidomethyl)phenyl]piperazine Hydrochloride M.p. 112°–114° C. Found: C, 52.69; H, 5.46; N, 8.40. $C_{29}H_{34}Cl_2N_4O_4S$.HCl.H$_2$O requires: C, 52.77; H, 5.65; N, 8.49%. m/e (ES$^+$) 605 (MH$^+$).

EXAMPLE 32

(S)-N-(2-{4-[2-Benzylamino-3-(3,4-dichlorobenzyloxy)propionyl]piperazin-1-yl}phenylmethyl)acetamide Dihydrochloride M.p. 122°–124° C. Found: C, 55.86; H, 5.76; N, 8.62. $C_{30}H_{34}Cl_2N_4O_3$.2HCl requires: C, 56.09; H, 5.65; N, 8.72%. m/e (ES$^+$) 569 (MH$^+$).

EXAMPLE 33

(S)-1-[2-Benzylamino-3-(3,4-dichlorobenzyloxy)propionyl]-4-[2-(dimethylaminomethyl)phenyl]piperazine Dihydrochloride M.p. 226°–228° C. Found: C, 56.43; H, 6.12; N, 8.99. $C_{30}H_{36}Cl_2N_4O_2$.2HCl.0.5H$_2$O requires: C, 56.52; H, 6.17; N, 8.79%. m/e (ES$^+$) 555 (MH$^+$).

EXAMPLE 34

(S)-1-[2-Benzylamino-3-(3,4-dichlorobenzyloxy)propionyl]-4-hydroxymethyl-4-phenylpiperidine Lithium borohydride (5.0 mg) was added to a stirred solution of (S)-methyl 1-[2-benzylamino-3-(3,4-dichlorobenzyloxy)propionyl]-4-phenylpiperidin-4-carboxylate (100 mg) in toluene (5.0 mL) and tetrahydrofuran (5.0 mL). The resulting solution was warmed to reflux for 3 h., cooled to room temperature and the solvent was evaporated under reduced pressure. The residue was partitioned between ethyl acetate and aqueous ammonium chloride (saturated) and the organic layer was separated, dried (MgSO$_4$) and the solvent was evaporated under reduced pressure. The residue was purified by MPLC on silica gel, eluting with CH$_2$Cl$_2$/MeOH/NH$_3$ (Aq.) (99:1:0.1) to give the title compound as a colorless solid (26 mg), $\delta_H$ (CDCl$_3$) 1.69–1.82 (5H, m), 2.41–2.61 (4H, m), 3.15–3.21 (2H m), 3.44 (2H, s), 3.53–3.68 (4H, m), 4.34 (1H br s), 6.98–7.46 (12H, m). m/e (ES$^+$) 527 (MH$^+$).

EXAMPLE 35

(S)-1'-[2-Benzylamino-3-(3,4-dichlorobenzyloxy) propionyl]spiro[2H-1-benzopyran-2,4'-piperidin]-4-(3H)-one Hydrochloride a) (S)-1'-[2-t-Butoxycarbonylamino-3-(3,4-dichlorobenzyloxy)propionyl]spiro[2H-1-benzopyran-2,4'-piperidin]-4-(3H)-one Triethylamine (0.50 mL, 0.36 g, 3.6 mmol) was added to a stirred, cooled (0° C.) mixture of (S)-2-t-butoxycarbonylamino-3-(3,4-dichlorobenzyloxy)propionic acid (364 mg, 1 mmol), spiro[2H-1-benzopyran-2,4'-piperidin]-4-(3H)-one hydrochloride (U.S. Pat. No. 5,206,240, Example 67A) (254 mg, 1 mmol), 1-(3-dimethylaminopropyl)-3-ethylcarbodiimide hydrochloride (230 mg, 1.2 mmol) and 1-hydroxybenzotriazole (162 mg, 1.2 mmol) in dimethylformamide (5 mL) and the mixture was stirred at room temperature for 2 h. Aqueous sodium hydrogen carbonate (saturated, 20 mL) and water (10 mL) were added and the mixture was extracted with ethyl acetate (3×20 mL). The combined organic fractions were washed with aqueous citric acid (10%, 2×20 mL), aqueous sodium hydrogen carbonate (saturated, 2×20 mL) and brine (20 mL), dried ($MgSO_4$) and the solvent was evaporated under reduced pressure. The residue was purified by flash column chromatography on silica gel, eluting with $CH_2Cl_2$/MeOH (99.5:0.5 increasing to 98:2) to give the title compound as a colorless foam (248 mg, 44%). m/e ($ES^+$) 563 ($MH^+$).

b) (S)-1'-[2-Benzylamino-3-(3,4-dichlorobenzyloxy) propionyl]spiro[2H-1-benzopyran-2,4'-piperidine]-4-(3H)-one Hydrochloride Methanolic hydrogen chloride (4M, 2 mL) was added to a stirred, cooled (0° C.) solution of (S)-1'-[2-t-butoxycarbonylamino-3-(3,4-dichlorobenzyloxy)propionyl] spiro[2H-1-benzopyran-2,4'-piperidine]-4-(3H)-one (243 mg, 0.43 mmol) in methanol (2 mL) and the mixture was stirred at room temperature for 5 h. The solvent was evaporated under reduced pressure, dichloromethane (5 mL), triethylamine (0.120 mL, 87 mg, 0.86 mmol), benzaldehyde (0.052 mL, 55 mg, 0.52 mmol) and magnesium sulfate (300 mg) were added. The mixture was stirred at room temperature for 4 h., filtered and the solvent was evaporated under reduced pressure. Methanol (5 mL) and sodium cyanoborohydride (54 mg, 0.86 mmol) were added. The mixture was stirred at room temperature for 1 h., aqueous sodium hydrogen carbonate (saturated, 20 mL) and water (10 mL) were added and the mixture was extracted with dichloromethane (3×20 mL). The combined organic fractions were dried ($MgSO_4$) and the solvent was evaporated under reduced pressure. Methanol (25 mL) was added and the volume was reduced to 10 mL by distillation. The remaining solvent was evaporated under reduced pressure and the residue was purified by flash column chromatography on silica gel, eluting with $CH_2Cl_2$/MeOH/$NH_3$ (Aq.) (99:1:0.1 increasing to 97:3:0.3). The residue was dissolved in methanol (5 mL), cooled to 0° C. and methanolic hydrogen chloride (1M, 0.23 mL) was added. The solvent was evaporated under reduced pressure and the residue was triturated with ether (5 mL). The solid was collected and dried in vacuo to give the title compound as a colorless solid (126 mg, 50%), mp. 173°–175° C. Found: C, 59.92; H, 5.14; N, 4.32. $C_{30}H_{30}Cl_2N_2O_4$.HCl.0.5$H_2O$ requires: C, 60.16; H, 5.39; N, 4.68%. m/e ($ES^+$) 553 ($MH^+$).

EXAMPLE 36

(2S, 4'RS)-1'-[2-Benzylamino-3-(3,4-dichlorobenzyloxy)propionyl]-3,4-dihydrospiro[2H-1-benzopyran-2,4'-piperidine]-4-ol Hydrochloride Methanolic hydrogen chloride (4M, 8 mL) was added to a stirred, cooled (0° C.) solution of (S)-1'-[2-t-butoxycarbonylamino-3-(3,4-dichlorobenzyloxy)propionyl] spiro[2H-1-benzopyran-2,4'-piperidine]-4-(3H)-one (899 mg, 1.6 mmol) in methanol (4 mL) and the mixture was stirred at room temperature for 16 h. The solvent was evaporated under reduced pressure, dichloromethane (10 mL), triethylamine (0.44 mL, 0.32 g, 3.2 mmol), benzaldehyde (0.195 mL, 203 mg, 1.9 mmol) and magnesium sulfate (1.0 g) were added. The mixture was stirred at room temperature for 4 h., filtered and the solvent was evaporated under reduced pressure. Methanol (10 mL) was added and the mixture was cooled in ice. Sodium borohydride (121 mg, 3.2 mmol) was added and the mixture was stirred at 0° C., adding further sodium borohydride (121 mg, 3.2 mmol) after 1 h. and 2 h. The mixture was stirred at room temperature for 16 h., aqueous sodium hydrogen carbonate (saturated, 40 mL) and water (20 mL) were added and the mixture was extracted with dichloromethane (3×40 mL). The combined organic fractions were dried ($MgSO_4$) and the solvent was evaporated under reduced pressure. The residue was dissolved in ethanol (10 mL) and cooled in ice. Sodium borohydride (121 mg, 3.2 mmol) was added and the mixture was stirred at 0° C., adding further sodium borohydride (121 mg, 3.2 mmol) after 2 h., 4 h. and 6 h. The mixture was stirred at room temperature for 14 h., aqueous sodium hydrogen carbonate (saturated, 40 mL) and water (20 mL) were added and the mixture was extracted with dichloromethane (3×40 mL). The combined organic fractions were dried ($MgSO_4$) and the solvent was evaporated under reduced pressure. The residue was purified by flash column chromatography on silica gel, eluting with $CH_2Cl_2$/MeOH/$NH_3$ (Aq.) (99:1:0.1 increasing to 98:2:0.2) to give (2S, 4'RS)-1'-[2-benzylamino-3-(3,4-dichlorobenzyloxy) propionyl]-3,4-dihydrospiro[2H-1-benzopyran-2,4'-piperidine]-4-ol as a colorless foam (491 mg, 55%), $δ_H$ ($CHCl_3$) 7.43–6.82 (12H, m), 4.92–4.34 (4H, m), 3.84–3.00 (8H, m), and 2.15–1.14 (8H, m). A sample (203 mg, 0.37 mmol) was dissolved in ethanol (5 mL), cooled to 0° C. and ethanolic hydrogen chloride (5M, 0.088 mL) was added. The solvent was evaporated under reduced pressure and the residue was triturated with ether (10 mL). The solid was collected and dried in vacuo to give the title compound as a colorless solid (218 mg, 100%), m.p. 116°–118° C. Found: C, 60.68; H, 5.77; N, 4.68. $C_{30}H_{32}Cl_2N_2O_4$.HCl requires: C, 60.87; H, 5.62; N, 4.73%. m/e ($ES^+$) 555 ($MH^+$).

EXAMPLE 37

(S)-1'-[2-Benzylamino-3-(3,4-dichlorobenzyloxy) propionyl]spiro[2H-1-benzopyran-2,4'-piperidine] Hydrochloride A mixture of (2S, 4'RS)-1'-[2-benzylamino-3-(3,4-dichlorobenzyloxy)propionyl]-3,4-dihydrospiro[2H-1-benzopyran-2,4'-piperidine]-4-ol (278 mg, 0.5 mmol) and p-toluenesulfonic acid monohydrate (114 mg, 0.6 mmol) in toluene was heated under reflux for 30 min. The mixture was cooled and the solvent was evaporated under reduced pressure. Aqueous sodium hydrogen carbonate (saturated, 20 mL) and water (10 mL) were added and the mixture was extracted with dichloromethane (3×20 mL). The combined organic fractions were dried ($MgSO_4$), the solvent was evaporated under reduced pressure and the residue was purified by MPLC on silica gel, eluting with $CH_2Cl_2$/MeOH/$NH_3$ (Aq.) (99:1:0.1). The residue was dissolved in ethanol (5 mL), cooled to 0° C. and ethanolic hydrogen chloride (5M, 0.098 mL) was added. The solvent was evaporated under reduced pressure and the residue was triturated with ether (10 mL). The solid was collected and dried in vacuo to give the title compound as a colorless solid (225 mg, 78%), m.p. 220°–222° C. Found: C, 62.74; H, 5.11; N, 4.83. $C_{30}H_{30}Cl_2N_2O_3$.HCl requires: C, 62.78; H, 5.44; N, 4.88%. m/e ($ES^+$) 537 ($MH^+$).

EXAMPLE 38

(S)-1-[2-Benzylamino-3-(3,4-dichlorobenzyloxy) propionyl]-4-(2-aminophenyl)piperazine Dihydrochloride Tin (II) chloride (1.79 g, 9.45 mmol) was added to a solution of (S)-1-[2-benzylamino-3-(3,4-dichlorobenzyloxy)propionyl]-4-(2-nitrophenyl)piperazine (1.03 g, 1.89 mmol) in ethanol (15 mL) and the mixture was stirred at 70° C. for 1 h. The solvent was evaporated under reduced pressure and the residue was diluted with ethyl acetate and washed with aqueous sodium hydroxide (2M, 3 x). The organic layer was dried ($MgSO_4$) and the solvent was evaporated under reduced pressure. The residue was purified by flash column chromatography on silica gel, eluting with $CH_2Cl_2$/MeOH/$NH_3$ (Aq.) (99:1:0.1) to give (S)-1-[2-benzylamino-3-(3,4-dichlorobenzyloxy)propionyl]-4-(2-aminophenyl)piperazine was a yellow oil (678 mg, 70%). A sample (70 mg) was dissolved in methanolic hydrogen chloride and the solvent was evaporated under reduced pressure. The residue was dissolved in acetonitrile/water (1:1) and freeze-dried to give the title compound as a colorless solid (70 mg); Found: C, 54.06; H, 5.42; N, 9.20. $C_{27}H_{30}Cl_2N_4O_2$.2HCl.0.5$H_2O$ requires: C, 54.47; H, 5.59; N, 9.41%. m/e ($ES^+$) 513 ($MH^+$).

We claim:

1. A compound of formula (I):

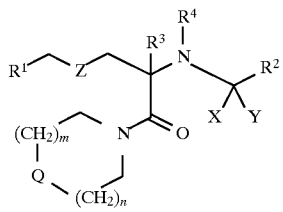

wherein m is zero, 1 or 2;

n is zero or 1, with proviso that the sum total of m+n is 2;

$R^1$ represents unsubstituted phenyl or phenyl substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, —O($CH_2$)$_p$O— where p is 1 or 2, halogen, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $COR^a$, $CO_2R^a$ or $CONR^aR^b$, where $R^a$ and $R^b$ each independently represent hydrogen, $C_{1-6}$alkyl, phenyl or trifluoromethyl; naphthyl; benzhydryl; or benzyl, where the naphthyl group or each phenyl moiety of benzyl and benzhydryl may be substituted by $C_{1-6}$alkyl, $C_{1-6}$alkoxy, halogen or trifluoromethyl;

$R^2$ represents hydrogen; unsubstituted phenyl or phenyl substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, —O($CH_2$)$_p$O— where p is 1 or 2, halogen, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $COR^a$, $CO_2R^a$ or $CONR^aR^b$, where $R^a$ and $R^b$ are as previously defined; heteroaryl selected from indazolyl, thienyl, furanyl, pyridyl, thiazolyl, tetrazolyl and quinolinyl; naphthyl; benzhydryl; or benzyl; wherein each heteroaryl, the naphthyl group and each phenyl moiety of benzyl and benzhydryl may be substituted by $C_{1-6}$alkyl, $C_{1-6}$alkoxy, halogen or trifluoromethyl;

$R^3$ and $R^4$ each independently represents hydrogen or $C_{1-6}$alkyl or $R^3$ and $R^4$ together are linked so as to form a $C_{1-3}$alkylene chain;

Q represents $CR^5R^6$;

X and Y each independently represents hydrogen, or together form a group =O;

Z represents a bond, O, S, SO, $SO_2$, $NR^c$ or —($CR^cR^d$)—, where $R^c$ and $R^d$ each independently represent hydrogen or $C_{1-6}$alkyl;

$R^5$ represents $C_{1-3}$alkyl substituted by a group selected from $OR^a$, $SR^a$, $SOR^a$, $SO_2R^a$, $NR^aR^b$, $NR^aCOR^b$, $NR^aCO_2R^b$, $NR^aSO_2R^b$, $COR^a$, $CO_2R^a$ or $CONR^aR^b$, where $R^a$ and $R^b$ are as previously defined; unsubstituted phenyl; phenyl substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, —O($CH_2$)$_p$O— where p is 1 or 2, halogen, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $NR^aSO_2R^b$, $COR^a$, $CO_2R^a$ or $CONR^aR^b$, or $C_{1-3}$alkyl substituted by a group selected from $OR^a$, $SR^a$, $SOR^a$, $SO_2R^a$, $NR^aR^b$, $NR^aCOR^b$, $NR^aCO_2R^b$, $NR^aSO_2R^b$, $COR^a$, $CO_2R^a$ or $CONR^aR^b$, where $R^a$ and $R^b$ are as previously defined; benzimidazol-1-yl; 2-ketobenzimidazol-1-yl; or heteroaryl selected from pyrindinyl, pyridazinyl, pyrimidinyl and pyrazinyl, wherein each heteroaryl may be substituted by $C_{1-6}$alkyl, $C_{1-6}$alkoxy, halogen or trifluoromethyl;

$R^6$ represent hydrogen, $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, halogen, cyano, nitro, trifluoromethyl, trimethylsilyl, $OR^a$, $SR^a$, $SOR^a$, $SO_2R^a$, $NR^aR^b$, $NR^aCOR^b$, $NR^aCO_2R^b$, $NR^aSO_2R^b$, $COR^a$, $CO_2R^a$, $CONR^aR^b$, or $C_{1-3}$alkyl substituted by a group selected from $OR^a$, $SR^a$, $SOR^a$, $SO_2R^a$, $NR^aR^b$, $NR^aCOR^b$, $NR^aCO_2R^b$, $NR^aSO_2R^b$, $COR^a$, $CO_2R^a$ or $CONR^aR^b$, where $R^a$ and $R^b$ are as previously defined;

or $R^5$ and $R^6$ together are linked so that $CR^5R^6$ represents a group selected from

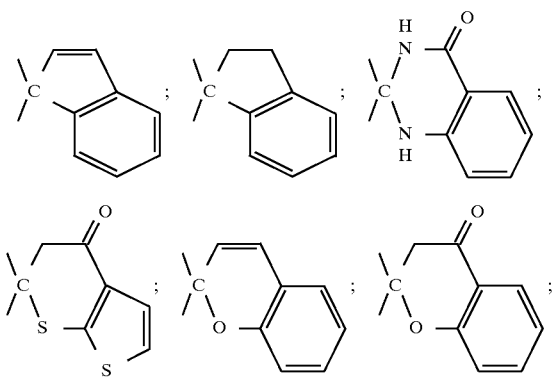

-continued

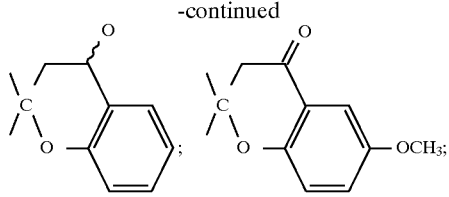

or a pharmaceutically acceptable salt thereof.

2. A process for the preparation of a compound as claimed in claim 1 which comprises:

(A), where X and Y are both hydrogen, reacting a compound of formula (II):

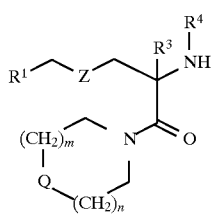

wherein R, $R^1$, $R^3$, $R^4$, $R^5$, Q, Z, m and n are as defined in claim 1, with an aldehyde of formula $R^2$—CHO in the presence of a reducing agent; or (B), where X and Y together form a group =O, reacting a compound of formula (II) with an acyl halide of formula $R^2$—COHal where Hal is a halogen atom; or (C), reacting a compound of formula (III) with a compound of formula (IV):

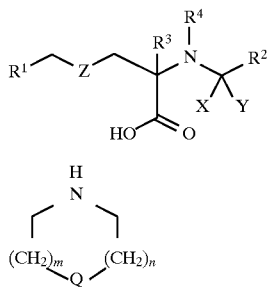

wherein R, $R^1$, $R^2$, $R^3$, $R^4$, $R^5$, Q, X, Y, Z, m and n are as defined in claim 1; or (D), interconversion of one compound of formula (I) into another compound of formula (I);

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

3. A compound as claimed in claim 1 wherein $R^1$ represents unsubstituted phenyl or phenyl substituted by one or two groups selected from $C_{1-6}$alkyl, halogen, and trifluoromethyl.

4. A compound as claimed in claim 1 wherein $R^2$ represents unsubstituted or substituted phenyl, 5-membered heteroaryl, 6-membered heteroaryl, quinolinyl, naphthyl, or benzhydryl.

5. A compound as claimed in claim 1 wherein $R^3$ and $R^4$ each independently represent hydrogen.

6. A compound a claimed in claim 1 wherein $R^5$ represents $C_{1-3}$alkyl substituted by a group selected from $NR^aCOR^b$, $NR^aSO_2R^b$ or $CO_2R^a$, where $R^a$ and $R^b$ are as defined in claim 1; unsubstituted phenyl; phenyl substituted by a group selected from $C_{1-6}$alkyl, halogen, cyano, nitro, $OR^a$, $NR^aR^b$, $NR^aSO_2R^b$ or $C_{1-3}$alkyl substituted by $NR^aR^b$, $NR^aCOR^b$ or $NR^aSO_2R^b$, where $R^a$ and $R^b$ are as defined in claim 1; 2-keto-benzimidazol-1-yl; pyridinyl; or pyrimidinyl.

7. A compound as claimed in claim 1 wherein $R^6$ represents hydrogen, cyano, $NR^aCOR^b$, $CO_2R^b$ or $C_{1-3}$alkyl substituted by $OR^a$, $NR^aCOR^b$ or $NRSO_2R^b$, where $R^a$ and $R^b$ are as defined in claim 1.

8. A compound as claimed in claim 1 wherein Q is $CR^5R^6$, wherein the group $CR^5R^6$ is selected from:

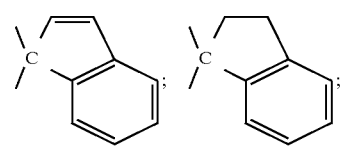

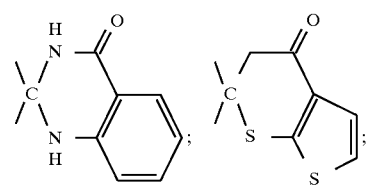

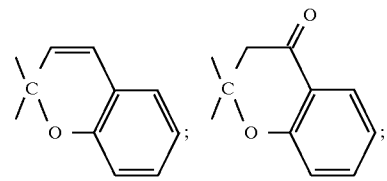

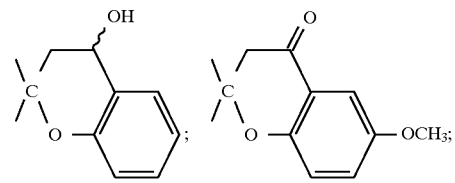

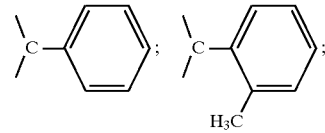

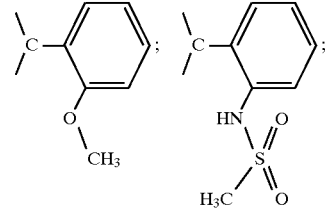

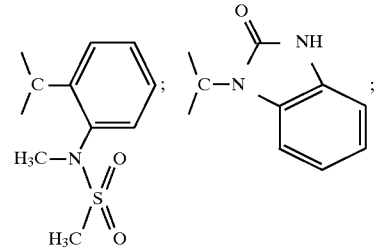

9. A compound as claimed in claim 1 wherein X and Y are both hydrogen atoms.

10. A compound as claimed in claim 1 wherein Z is an oxygen atom.

11. A compound as claimed in claim 1 of formula (Ia):

wherein m, n, Q, X and Y are as defined in claim 1;

Z' is O, S or —CH$_2$—;

R$^{20}$ and R$^{21}$ independently represent hydrogen, C$_{1-6}$alkyl, halogen, trifluoromethyl, OR$^a$, or NR$^a$R$^b$, where R$^a$ and R$^b$ are as defined in claim 1; and R$^{22}$ and R$^{23}$ independently represent hydrogen or halogen;

or a pharmaceutically acceptable salt thereof.

12. A compound as claimed in claim 1 of formula (Ib):

wherein m, n, Q, X and Y are as defined in claim 1;

Z" is O or —CH$_2$—;

R$^{24}$ and R$^{25}$ independently represent hydrogen or chlorine; and

R$^{26}$ and R$^{27}$ independently represent hydrogen or chlorine, with the proviso that at least one of R$^{26}$ and R$^{27}$ represents chlorine;

or a pharmaceutically acceptable salt thereof.

13. A compound selected from:

(S)-1-[2-benzylamino-3-(3,4-dichlorobenzyloxy)propionyl]-4-(2-keto-1-benzimidazolinyl)piperidine;

(S)-1'-[3-benzyloxy-2-(3,4-dichlorobenzylamino)propionyl]spiro[1H-indene-1,4'-piperidine];

(S)-N-({1-[3-benzyloxy-2-(3,4-dichlorobenzylamino)propionyl]-4-phenylpiperidin-4-yl}methyl)acetamide;

(S)-1-[3-benzyloxy-2-(3,4-dichlorobenzylamino)propionyl]-4-(methanesulfonamidomethyl)-4-phenylpiperidine;

(S)-1-[3-benzyloxy-2-(3,4-dichlorobenzylamino)propionyl]-4-phenylpiperidine;

(S)-N-{1-[3-benzyloxy-2-(3,4-dichlorobenzylamino)propionyl]-4-phenylpiperidin-4-yl}acetamide;

(S)-1-[2-benzylamino-3-(3,4-dichlorobenzyloxy)propionyl]-4-cyano-4-phenylpiperidine;

(S)-methyl 1-[2-benzylamino-3-(3,4-dichlorobenzyloxy)propionyl]-4-phenylpiperidine-4-carboxylate;

(S)-1-[2-benzylamino-3-(3,4-dichlorobenzyloxy)propionyl]-4-(2-methoxyphenyl)piperidine;

(S)-1-[2-benzylamino-3-(3,4-dichlorobenzyloxy)propionyl]-4-[2-(methanesulfonamido)phenyl]piperidine;

(S)-1-[2-benzylamino-3-(3,4-dichlorobenzyloxy)propionyl]-4-{2-[N-(methyl)methanesulfonamido]phenyl}piperidine;

(S)-1-[2-benzylamino-3-(3,4-dichlorobenzyloxy)propionyl]-4-(methanesulfonamidomethyl)-4-phenylpiperidine;

(S)-1-[2-benzylamino-3-(3,4-dichlorobenzyloxy)propionyl]-4-(N-phenylmethanesulfonamidomethyl)piperidine;

(S)-N-({1-[2-benzylamino-3-(3,4-dichlorobenzyloxy)propionyl]-4-phenylpiperidin-4-yl}methyl)acetamide;

(S)-N-({1-[2-benzylamino-3-(3,4-dichlorobenzyloxy)propionyl]piperidin-4-yl}methyl)-N-phenylacetamide;

(S)-1-[2-benzylamino-3-(3,4-dichlorobenzyloxy)propionyl]spiro[piperidine-4,2'(1'H)-quinazolin]-4'(3'H)-one];

(S)-1'-[2-benzylamino-3-(3,4-dichlorobenzyloxy)propionyl]-2,3-dihydrospiro[1H-indene-1,4'-piperidine];

(S)-1-[2-benzylamino-3-(3,4-dichlorobenzyloxy)propionyl]spiro[piperidine-4,6'-[6'H]thieno[2,3-b]thiopyran]-4'(5'H)-one];

(2S, 3'RS)-1'-[2-benzylamino-3-(3,4-dichlorobenzyloxy)propionyl]spiro[2H-1-benzopyran-2,3'-piperidine]-4-(3H)-one;

(S)-1'-[2-benzylamino-3-(3,4-dichlorobenzyloxy)propionyl]-6-methoxyspiro[2H-1-benzopyran-2,4'-piperidine]-4-(3H)-one;

(S)-1-[2-benzylamino-3-(3,4-dichlorobenzyloxy)propionyl]-4-(2-methylphenyl)piperidine;

(S)-1-[2-benzylamino-3-(3,4-dichlorobenzyloxy)propionyl]-4-hydroxymethyl-4-phenylpiperidine;

(S)-1'-[2-benzylamino-3-(3,4-dichlorobenzyloxy)propionyl]spiro[2H-1-benzopyran-2,4'-piperidin]-4-(3H)-one;

(2S, 4'RS)-1'-[2-benzylamino-3-(3,4-dichlorobenzyloxy)propionyl]-3,4-dihydrospiro[2H-1-benzopyran-2,4'-piperidine]-4-ol;

(S)-1'-[2-benzylamino-3-(3,4-dichlorobenzyloxy)propionyl]spiro[2H-1-benzopyran-2,4'-piperidine];

or a pharmaceutically acceptable salt thereof.

14. A pharmaceutical composition comprising a compound as claimed in claim 1 in association with a pharmaceutically acceptable carrier or excipient.

15. A method for the treatment or prevention of physiological disorders associated with an excess of tachykinins, which method comprises administration to a patient in need thereof of a tachykinin reducing amount of a compound according to claim 1.

16. A method according to claim 15 for the treatment or prevention of pain or inflammation.

17. A method according to claim 15 for the treatment or prevention of migraine.

18. A method according to claim 15 for the treatment or prevention of emesis.

19. A method according to claim 15 for the treatment or prevention of postherpetic neuralgia.

* * * * *